United States Patent
Sheffield et al.

(10) Patent No.: US 7,565,199 B2
(45) Date of Patent: Jul. 21, 2009

(54) METHODS FOR TREATING AND/OR COLLECTING INFORMATION REGARDING NEUROLOGICAL DISORDERS, INCLUDING LANGUAGE DISORDERS

(75) Inventors: Warren Douglas Sheffield, Seattle, WA (US); Alvaro Pascual-Leone, Wayland, MA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 146 days.

(21) Appl. No.: 10/731,892

(22) Filed: Dec. 9, 2003

(65) Prior Publication Data

US 2005/0033378 A1 Feb. 10, 2005

Related U.S. Application Data

(60) Provisional application No. 60/432,073, filed on Dec. 9, 2002, provisional application No. 60/515,309, filed on Oct. 28, 2003.

(51) Int. Cl.
*A61N 1/32* (2006.01)
*A61B 5/05* (2006.01)
(52) U.S. Cl. .............................. 607/45; 607/50; 600/411
(58) Field of Classification Search ................. 607/1–3, 607/45–46, 62, 50; 600/409–420, 544–545
See application file for complete search history.

(56) References Cited

U.S. PATENT DOCUMENTS

| | | | |
|---|---|---|---|
| 2,716,226 A | 8/1955 | Jonas | |
| 2,721,316 A | 10/1955 | Shaw | |
| 3,628,193 A | 12/1971 | Collins | |
| 3,650,276 A | 3/1972 | Burghele et al. | |
| 3,850,161 A | 11/1974 | Liss | |
| 3,918,461 A | 11/1975 | Cooper | |
| 4,019,518 A | 4/1977 | Maurer et al. | |
| 4,030,509 A | 6/1977 | Heilman et al. | |

(Continued)

FOREIGN PATENT DOCUMENTS

DE 19750043 5/1999

(Continued)

OTHER PUBLICATIONS

Cao, Y. et al. "Cortical Language Activation in Stroke Patient's Recovering From Aphasia With Functional MRI," Journal of the American Heart Association, Print ISSN: 0039-2499. Online ISSN: 1524-4628. 99. 2331-2340, (Nov. 1999).*

(Continued)

*Primary Examiner*—Carl H Layno
*Assistant Examiner*—Jessica Reidel
(74) *Attorney, Agent, or Firm*—Perkins Coie LLP

(57) ABSTRACT

Methods for treating and/or collecting information regarding neurological disorders, including language disorders. A method in accordance with one embodiment directing a patient to perform a language-based task, directing information to be collected, with the information corresponding to a level of neural activity in the patient's brain while the patient performs the language-based task, and, based at least in part on the information, selecting a stimulation site within the patient's skull for receiving an electrode coupleable to an electrical current. In further embodiments, at least one electrode can be placed at the stimulation site, and the patient's language disorder can be reduced by applying electrical stimulation directly to the stimulation site via the at least one electrode.

57 Claims, 6 Drawing Sheets

U.S. PATENT DOCUMENTS

| | | |
|---|---|---|
| 4,125,116 A | 11/1978 | Fischell |
| 4,140,133 A | 2/1979 | Kastrubin et al. |
| 4,214,804 A | 7/1980 | Little |
| 4,245,645 A | 1/1981 | Picard et al. |
| 4,308,868 A | 1/1982 | Jhabvala |
| 4,328,813 A | 5/1982 | Ray |
| 4,340,038 A | 7/1982 | McKean |
| 4,390,023 A | 6/1983 | Rise |
| 4,431,000 A | 2/1984 | Butler et al. |
| 4,474,186 A | 10/1984 | Ledley et al. |
| 4,541,432 A | 9/1985 | Molina-Negro et al. |
| 4,542,752 A | 9/1985 | DeHaan et al. |
| 4,590,946 A | 5/1986 | Loeb |
| 4,607,639 A | 8/1986 | Tanagho et al. |
| 4,646,744 A | 3/1987 | Capel |
| 4,702,254 A | 10/1987 | Zabara |
| 4,817,634 A | 4/1989 | Holleman et al. |
| 4,844,075 A | 7/1989 | Liss et al. |
| 4,865,048 A | 9/1989 | Eckerson |
| 4,869,255 A | 9/1989 | Putz |
| 4,903,702 A | 2/1990 | Putz |
| 4,969,468 A | 11/1990 | Byers et al. |
| 5,002,053 A | 3/1991 | Garcia-Rill et al. |
| 5,024,226 A | 6/1991 | Tan |
| 5,031,618 A | 7/1991 | Mullett |
| 5,044,368 A | 9/1991 | Putz |
| 5,054,906 A | 10/1991 | Lyons |
| 5,063,932 A | 11/1991 | Dahl et al. |
| 5,092,835 A | 3/1992 | Schurig et al. |
| 5,119,832 A | 6/1992 | Xavier |
| 5,121,754 A | 6/1992 | Mullett |
| 5,143,089 A | 9/1992 | Alt |
| 5,169,384 A | 12/1992 | Bosniak et al. |
| 5,184,620 A | 2/1993 | Cudahy et al. |
| 5,193,540 A | 3/1993 | Schulman et al. |
| 5,215,086 A | 6/1993 | Terry, Jr. et al. |
| 5,215,088 A | 6/1993 | Normann et al. |
| 5,224,491 A | 7/1993 | Mehra |
| 5,255,678 A | 10/1993 | Deslauriers et al. |
| 5,263,967 A | 11/1993 | Lyons |
| 5,269,303 A | 12/1993 | Wernicke et al. |
| 5,271,417 A | 12/1993 | Swanson et al. |
| 5,282,468 A | 2/1994 | Klepinski |
| 5,299,569 A | 4/1994 | Wernicke et al. |
| 5,303,705 A | 4/1994 | Nenov |
| 5,304,206 A | 4/1994 | Baker, Jr. et al. |
| 5,314,458 A | 5/1994 | Najafi et al. |
| 5,358,513 A | 10/1994 | Powell, III et al. |
| 5,358,514 A | 10/1994 | Schulman et al. |
| 5,370,672 A | 12/1994 | Fowler et al. |
| 5,405,375 A | 4/1995 | Ayers et al. |
| 5,406,957 A | 4/1995 | Tansey |
| 5,411,540 A | 5/1995 | Edell et al. |
| 5,417,719 A | 5/1995 | Hull et al. |
| 5,423,864 A | 6/1995 | Ljungstroem |
| 5,423,877 A | 6/1995 | Mackey |
| 5,441,528 A | 8/1995 | Chang et al. |
| 5,458,631 A | 10/1995 | Xavier |
| 5,464,446 A | 11/1995 | Dreessen et al. |
| 5,520,190 A | 5/1996 | Benedict et al. |
| 5,522,864 A | 6/1996 | Wallace et al. |
| 5,537,512 A | 7/1996 | Hsia et al. |
| 5,540,734 A | 7/1996 | Zabara |
| 5,540,736 A | 7/1996 | Haimovish et al. |
| 5,549,655 A | 8/1996 | Erickson |
| 5,562,708 A | 10/1996 | Combs et al. |
| 5,575,813 A | 11/1996 | Edell |
| 5,591,216 A | 1/1997 | Testerman et al. |
| 5,593,432 A | 1/1997 | Crowther et al. |
| 5,601,611 A | 2/1997 | Fayram et al. |
| 5,611,350 A | 3/1997 | John |
| 5,618,531 A | 4/1997 | Cherksey |
| 5,628,317 A | 5/1997 | Starkebaum et al. |
| 5,674,251 A | 10/1997 | Combs et al. |
| 5,674,264 A | 10/1997 | Carter et al. |
| 5,676,655 A | 10/1997 | Howard, III et al. |
| 5,683,422 A | 11/1997 | Rise |
| 5,702,429 A | 12/1997 | King |
| 5,707,334 A | 1/1998 | Young |
| 5,711,316 A | 1/1998 | Elsberry et al. |
| 5,713,922 A | 2/1998 | King |
| 5,713,923 A | 2/1998 | Ward et al. |
| 5,716,377 A | 2/1998 | Rise et al. |
| 5,722,401 A | 3/1998 | Pietroski et al. |
| 5,735,814 A | 4/1998 | Elsberry et al. |
| 5,750,376 A | 5/1998 | Weiss et al. |
| 5,752,979 A | 5/1998 | Benabid |
| 5,753,505 A | 5/1998 | Luskin |
| 5,769,778 A | 6/1998 | Abrams et al. |
| 5,772,591 A | 6/1998 | Cram |
| 5,782,798 A | 7/1998 | Rise |
| 5,782,873 A | 7/1998 | Collins |
| 5,792,186 A | 8/1998 | Rise |
| 5,797,970 A | 8/1998 | Pouvreau |
| 5,814,014 A | 9/1998 | Elsberry et al. |
| 5,814,092 A | 9/1998 | King |
| 5,824,021 A | 10/1998 | Rise |
| 5,824,030 A | 10/1998 | Yang et al. |
| 5,832,932 A | 11/1998 | Elsberry et al. |
| 5,833,603 A | 11/1998 | Kovacs et al. |
| 5,833,709 A | 11/1998 | Rise et al. |
| 5,843,148 A | 12/1998 | Gijsbers |
| 5,843,150 A | 12/1998 | Dreessen et al. |
| 5,846,196 A | 12/1998 | Siekmeyer et al. |
| 5,865,842 A | 2/1999 | Knuth et al. |
| 5,871,517 A | 2/1999 | Abrams et al. |
| 5,885,976 A | 3/1999 | Sandyk |
| 5,886,769 A | 3/1999 | Zolten |
| 5,893,883 A | 4/1999 | Torgerson et al. |
| 5,904,916 A | 5/1999 | Hirsch |
| 5,913,882 A | 6/1999 | King |
| 5,916,171 A | 6/1999 | Mayevsky |
| 5,925,070 A | 7/1999 | King et al. |
| 5,928,144 A | 7/1999 | Real |
| 5,938,688 A | 8/1999 | Schiff |
| 5,938,689 A | 8/1999 | Fischell et al. |
| 5,941,906 A | 8/1999 | Barreras et al. |
| 5,964,794 A | 10/1999 | Bolz et al. |
| 5,975,085 A | 11/1999 | Rise |
| 5,978,702 A | 11/1999 | Ward et al. |
| 5,983,140 A | 11/1999 | Smith et al. |
| 6,006,124 A | 12/1999 | Fischell et al. |
| 6,011,996 A | 1/2000 | Gielen et al. |
| 6,016,449 A | 1/2000 | Fischell et al. |
| 6,018,682 A | 1/2000 | Rise |
| 6,021,352 A | 2/2000 | Christopherson et al. |
| 6,024,702 A | 2/2000 | Iversen |
| 6,026,326 A | 2/2000 | Bardy |
| 6,035,236 A | 3/2000 | Jarding et al. |
| 6,038,480 A | 3/2000 | Hrdlicka et al. |
| 6,040,180 A | 3/2000 | Johe |
| 6,042,579 A | 3/2000 | Elsberry et al. |
| 6,051,017 A | 4/2000 | Loeb et al. |
| 6,052,624 A | 4/2000 | Mann |
| 6,055,456 A | 4/2000 | Gerber |
| 6,057,846 A | 5/2000 | Sever, Jr. |
| 6,057,847 A | 5/2000 | Jenkins |
| 6,058,331 A | 5/2000 | King |
| 6,060,048 A | 5/2000 | Cherksey |
| 6,061,593 A | 5/2000 | Fischell et al. |
| 6,066,163 A | 5/2000 | John |
| 6,094,598 A | 7/2000 | Elsberry et al. |
| 6,095,148 A | 8/2000 | Shastri et al. |
| 6,104,956 A | 8/2000 | Naritoku et al. |

| | | | | | | |
|---|---|---|---|---|---|---|
| 6,104,960 | A | 8/2000 | Duysens et al. | 6,687,525 B2 | 2/2004 | Llinas |
| 6,122,548 | A | 9/2000 | Starkebaum et al. | 6,690,974 B2 | 2/2004 | Archer |
| 6,126,657 | A | 10/2000 | Edwards et al. | 6,708,064 B2 | 3/2004 | Rezai |
| 6,128,527 | A | 10/2000 | Howard, III et al. | 6,725,094 B2 | 4/2004 | Saberski |
| 6,128,537 | A | 10/2000 | Rise | 6,731,978 B2 | 5/2004 | Olsen et al. |
| 6,128,538 | A | 10/2000 | Fischell et al. | 6,764,498 B2 | 7/2004 | Mische |
| 6,129,685 | A | 10/2000 | Howard, III | 6,782,292 B2 | 8/2004 | Whitehurst |
| 6,134,474 | A | 10/2000 | Fischell et al. | 6,788,975 B1 | 9/2004 | Whitehurst et al. |
| 6,149,612 | A | 11/2000 | Schnapp | 6,795,737 B2 | 9/2004 | Gielen et al. |
| 6,152,143 | A | 11/2000 | Edwards | 6,810,286 B2 | 10/2004 | Donovan et al. |
| 6,161,044 | A | 12/2000 | Silverstone | 6,839,594 B2 | 1/2005 | Cohen et al. |
| 6,161,045 | A | 12/2000 | Fischell et al. | 6,850,802 B2 | 2/2005 | Holsheimer et al. |
| 6,161,047 | A | 12/2000 | King et al. | 6,873,872 B2 | 3/2005 | Gluckman et al. |
| 6,176,242 | B1 | 1/2001 | Rise | 6,892,097 B2 | 5/2005 | Holsheimer |
| 6,190,893 | B1 | 2/2001 | Shastri et al. | 6,895,280 B2 | 5/2005 | Meadows et al. |
| 6,198,958 | B1 | 3/2001 | Ives et al. | 6,898,464 B2 | 5/2005 | Edell et al. |
| 6,205,360 | B1 | 3/2001 | Carter et al. | 6,907,296 B1 | 6/2005 | Doan et al. |
| 6,205,361 | B1 | 3/2001 | Kuzma et al. | 6,922,590 B1 | 7/2005 | Whitehurst |
| 6,210,417 | B1 | 4/2001 | Baudino et al. | 6,934,580 B1 | 8/2005 | Osorio et al. |
| 6,221,908 | B1 | 4/2001 | Kilgard et al. | 6,944,497 B2 * | 9/2005 | Stypulkowski ................ 607/2 |
| 6,227,203 | B1 | 5/2001 | Rise et al. | 6,944,501 B1 | 9/2005 | Pless |
| 6,230,049 | B1 | 5/2001 | Fischell et al. | 6,949,081 B1 | 9/2005 | Chance |
| 6,236,892 | B1 | 5/2001 | Feler | 6,959,215 B2 * | 10/2005 | Gliner et al. ................ 607/45 |
| 6,246,912 | B1 | 6/2001 | Sluijter et al. | 6,990,377 B2 | 1/2006 | Gliner et al. |
| 6,251,115 | B1 | 6/2001 | Williams et al. | 7,006,859 B1 | 2/2006 | Osorio et al. |
| 6,263,225 | B1 | 7/2001 | Howard, III | 7,010,351 B2 * | 3/2006 | Firlik et al. ................ 607/45 |
| 6,263,237 | B1 | 7/2001 | Rise | 7,015,816 B2 | 3/2006 | Wildman et al. |
| 6,280,462 | B1 | 8/2001 | Hauser et al. | 7,024,247 B2 | 4/2006 | Gliner et al. |
| 6,301,493 | B1 | 10/2001 | Marro et al. | 7,050,856 B2 | 5/2006 | Stypulkowski |
| 6,304,787 | B1 | 10/2001 | Kuzma et al. | 7,065,412 B2 | 6/2006 | Swoyer |
| 6,319,241 | B1 | 11/2001 | King et al. | 7,107,097 B2 | 9/2006 | Stern et al. |
| 6,339,725 | B1 | 1/2002 | Naritoku et al. | 7,107,104 B2 | 9/2006 | Keravel et al. |
| 6,353,754 | B1 | 3/2002 | Fischell et al. | 7,146,222 B2 | 12/2006 | Boling |
| 6,354,299 | B1 | 3/2002 | Fischell et al. | 7,149,586 B2 | 12/2006 | Greenberg et al. |
| 6,356,786 | B1 | 3/2002 | Rezai et al. | 7,184,840 B2 | 2/2007 | Stolz et al. |
| 6,356,792 | B1 | 3/2002 | Errico et al. | 7,187,968 B2 | 3/2007 | Wolf et al. |
| 6,360,122 | B1 | 3/2002 | Fischell et al. | 7,187,977 B2 | 3/2007 | Paul, Jr. |
| 6,366,813 | B1 | 4/2002 | DiLorenzo | 7,191,018 B2 | 3/2007 | Gielen et al. |
| 6,375,666 | B1 | 4/2002 | Mische | 7,346,395 B2 | 3/2008 | Lozano et al. |
| 6,405,079 | B1 | 6/2002 | Ansarinia | 2002/0028072 A1 | 3/2002 | Kashiyama |
| 6,418,344 | B1 | 7/2002 | Rezai | 2002/0087201 A1 | 7/2002 | Firlik |
| 6,425,852 | B1 | 7/2002 | Epstein et al. | 2002/0091419 A1 | 7/2002 | Firlik et al. |
| 6,427,086 | B1 | 7/2002 | Fischell et al. | 2002/0099295 A1 | 7/2002 | Gil et al. |
| 6,456,886 | B1 | 9/2002 | Howard, III et al. | 2002/0099412 A1 | 7/2002 | Fischell et al. |
| 6,459,936 | B2 | 10/2002 | Fischell et al. | 2002/0138101 A1 | 9/2002 | Suda et al. |
| 6,463,328 | B1 | 10/2002 | John | 2002/0169485 A1 | 11/2002 | Pless et al. |
| 6,464,356 | B1 | 10/2002 | Sabel et al. | 2003/0074032 A1 | 4/2003 | Gliner |
| 6,466,822 | B1 | 10/2002 | Pless | 2003/0078633 A1 | 4/2003 | Firlik et al. |
| 6,473,568 | B2 | 10/2002 | Kashiyama | 2003/0088274 A1 | 5/2003 | Gliner et al. |
| 6,473,639 | B1 | 10/2002 | Fischell et al. | 2003/0097161 A1 | 5/2003 | Firlik et al. |
| 6,480,743 | B1 | 11/2002 | Kirkpatrick et al. | 2003/0114886 A1 | 6/2003 | Gluckman et al. |
| 6,484,059 | B2 | 11/2002 | Gielen | 2003/0125786 A1 | 7/2003 | Gliner et al. |
| 6,487,450 | B1 | 11/2002 | Chen | 2003/0130706 A1 | 7/2003 | Sheffield et al. |
| 6,497,699 | B1 | 12/2002 | Ludvig et al. | 2003/0149457 A1 | 8/2003 | Tcheng et al. |
| 6,499,488 | B1 | 12/2002 | Hunter et al. | 2003/0176901 A1 | 9/2003 | May |
| 6,505,075 | B1 | 1/2003 | Weiner | 2003/0187490 A1 | 10/2003 | Gliner |
| 6,507,755 | B1 | 1/2003 | Gozani et al. | 2004/0073270 A1 | 4/2004 | Firlik et al. |
| 6,529,774 | B1 | 3/2003 | Greene | 2004/0082847 A1 * | 4/2004 | McDermott ................ 600/410 |
| 6,539,263 | B1 | 3/2003 | Schiff et al. | 2004/0088024 A1 | 5/2004 | Firlik et al. |
| 6,549,814 | B1 | 4/2003 | Strutz et al. | 2004/0092809 A1 | 5/2004 | DeCharms |
| 6,556,868 | B2 | 4/2003 | Naritoku et al. | 2004/0102828 A1 | 5/2004 | Lowry et al. |
| 6,569,654 | B2 | 5/2003 | Shastri et al. | 2004/0111127 A1 | 6/2004 | Gliner et al. |
| 6,591,138 | B1 | 7/2003 | Fischell et al. | 2004/0131998 A1 | 7/2004 | Marom et al. |
| 6,597,954 | B1 | 7/2003 | Pless et al. | 2004/0138550 A1 | 7/2004 | Hartlep et al. |
| 6,609,030 | B1 | 8/2003 | Rezai et al. | 2004/0158298 A1 | 8/2004 | Gliner |
| 6,615,065 | B1 | 9/2003 | Barrett et al. | 2004/0176831 A1 | 9/2004 | Gliner et al. |
| 6,622,048 | B1 | 9/2003 | Mann | 2004/0181263 A1 | 9/2004 | Balzer et al. |
| 6,631,295 | B2 | 10/2003 | Rubinstein et al. | 2004/0236388 A1 | 11/2004 | Gielen et al. |
| 6,633,780 | B1 | 10/2003 | Berger | 2004/0249422 A1 | 12/2004 | Gliner et al. |
| 6,647,296 | B2 | 11/2003 | Fischell et al. | 2005/0004620 A1 | 1/2005 | Singhal et al. |
| 6,658,299 | B1 | 12/2003 | Dobelle | 2005/0015129 A1 | 1/2005 | Mische |
| 6,665,562 | B2 | 12/2003 | Gluckman et al. | 2005/0021104 A1 | 1/2005 | DiLorenzo |
| 6,684,105 | B2 | 1/2004 | Cohen et al. | 2005/0021105 A1 | 1/2005 | Firlik et al. |

| | | |
|---|---|---|
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0096701 A1 | 5/2005 | Donovan et al. |
| 2005/0113882 A1 | 5/2005 | Cameron et al. |
| 2005/0119712 A1 | 6/2005 | Shafer |
| 2005/0154425 A1 | 7/2005 | Boveja et al. |
| 2005/0154426 A1 | 7/2005 | Boveja et al. |
| 2005/0182453 A1 | 8/2005 | Whitehurst |
| 2005/0228451 A1 | 10/2005 | Jaax et al. |
| 2006/0004422 A1 | 1/2006 | De Ridder |
| 2006/0004423 A1 | 1/2006 | Boveja et al. |
| 2006/0015153 A1 | 1/2006 | Gliner et al. |
| 2006/0095088 A1 | 5/2006 | De Ridder |
| 2006/0106430 A1 | 5/2006 | Fowler et al. |
| 2006/0106431 A1 | 5/2006 | Wyler et al. |
| 2006/0129205 A1 | 6/2006 | Boveja et al. |
| 2006/0173522 A1 | 8/2006 | Osorio |
| 2006/0217782 A1 | 9/2006 | Boveja et al. |
| 2006/0241717 A1 | 10/2006 | Whitehurst et al. |
| 2007/0032834 A1 | 2/2007 | Gliner et al. |
| 2007/0055320 A1 | 3/2007 | Weinand |
| 2007/0060974 A1 | 3/2007 | Lozano |
| 2007/0088403 A1 | 4/2007 | Wyler et al. |
| 2007/0088404 A1 | 4/2007 | Wyler et al. |
| 2007/0100398 A1 | 5/2007 | Sloan |
| 2007/0100598 A1 | 5/2007 | Zeidman |
| 2007/0179534 A1 | 8/2007 | Firlik et al. |
| 2007/0179558 A1 | 8/2007 | Gliner et al. |
| 2008/0045775 A1 | 2/2008 | Lozano |
| 2008/0139870 A1 | 6/2008 | Gliner et al. |

FOREIGN PATENT DOCUMENTS

| | | |
|---|---|---|
| EP | 0214527 | 3/1987 |
| EP | 0319844 | 6/1989 |
| EP | 0 998 958 A2 | 10/2000 |
| EP | 1145736 | 10/2001 |
| EP | 1180056 | 11/2003 |
| WO | WO 87/07511 | 12/1987 |
| WO | WO 94/07564 | 4/1994 |
| WO | WO 95/21591 | 8/1995 |
| WO | WO-9745160 | 12/1997 |
| WO | WO 98/06342 | 2/1998 |
| WO | WO 01/97906 | 12/2001 |
| WO | WO 02/09811 | 2/2002 |
| WO | WO 02/36003 | 5/2002 |
| WO | WO 02/38031 | 5/2002 |
| WO | WO 02/38217 | 5/2002 |
| WO | WO 03/082402 | 3/2003 |
| WO | WO 03/043690 | 5/2003 |
| WO | WO-03/101532 | 12/2003 |

OTHER PUBLICATIONS

Binder, Jeffrey, MD "Functional Magnetic Resonance Imaging: Language Mapping." Neurosurgery Clinics of North America 8.3 (1997): 383-392.*
Schäffler et al. "Quantitative Comparison of Language Deficits Produced by Extraoperative electrical Stimulation of Broca's, Wernicke's, and Basal Temporal Language Areas" Epilepsia 37(5) (1996) 463-475.*
U.S. Appl. No. 60/325,872, Sheffield.
U.S. Appl. No. 60/325,978, Gliner.
Bel, S. and Bauer, B.L., "Dorsal Column Stimulation (DCS): Cost to Benefit Analysis," Acta Neurochirurgica, Suppl. 52, pp. 121-123 (1991).
Benabid, A.L. et al, "Chronic electrical stimulation of the ventralis intermedius nucleus of the thalamus as a treatment of movement disorders," J. Neurosurg., Apr. 1997, 86(4); 737; http://www.ncbi.nlm.nih.gov; [accessed Nov. 18, 2003].
Butefisch et al., "Mechanisms of use-dependent plasticity in the human motor cortex," Proc. Natl. Acad. Sci. USA, vol. 97, No. 7, pp. 3661-3665 (Mar. 2000).
Canavero, S. and Paolotti, R., "Extradural Motor Cortex Stimulation afor Advanced Parkinson's Disease: Case Report," Movement Disorders, 15(1):169-171,2000.
Cincotta et al., "Reorganization of the motor cortex in a patient with congenital hemiparesis and mirror movements," Neurology, vol. 55, pp. 129-131 (2000).
Classen, et al., "Rapid Plasticity of Human Cortical Movement Representation Induced by Practice," The Journal of Neurophysiology, vol. 79, No. 2, pp. 1117-1123 (Feb. 1998).
Cohen et al., "Studies of Neuroplasticity With Transcranial Magnetic Stimulation," The Journal of Clinical Neurophysiology, vol. 15, No. 4 (1998).
Cramer, S.C. and Bastings, E.P., "Mapping clinically relevant plasticity after stroke," Neuropharmacology vol. 19, No. 5, pp. 842-851 (Apr. 2000).
Dam et al., "Effects of Fluoxetine and Maprotiline on Functional Recovery in Poststroke Hemiplegic Patients Undergoing Rehabilitation Therapy," Stroke, vol. 27, No. 7, pp. 1211-1214 (Jul. 1996).
Feys et al., "Value of somatosensory and motor evoked potentials in predicting arm recovery after a stroke," (Oct. 1999).
Franzini et al., "Reversal of thalamic hand syndrome by long-term motor cortex stimulation," Journal of Neurosurgery 93:873-875 (2000).
Gladstone et al., "Enhancing Recovery after Stroke with Noradrenergic Pharmacotherapy: A New Frontier?," Can J. Neurol. Sci., vol. 27, No. 2 (May 2000).
Gordon et al., "Parameters for direct cortical electrical stimulation in the human: histopathologic confirmation," Electroencephalography and clinical Neurophysiology, vol. 75, pp. 371-377 (1990).
Hodge, Jr., C.J. and Boakye, M., "Biological Plasticity: The Future of Science in Neurosurgery," Neurosurgery, vol. 48, No. 1 (Jan. 2001).
Kauhanen et al., "Domans and Determinants of Quality of Life After Stroke Caused by Brian Infarction," Arch. Phys. Med. Rehabil., vol. 81, pp. 1541-1546 (Dec. 2000).
Kopell et al., "The Continuing Evolution of Psychiatric Neurosurgery," CNS Spectrums, vol. 5, No. 10, pp. 20-31 (Oct. 2000).
Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No.1 , pp. 4-7 (2001).
Liepert et al., "Treatment-Induced Cortical Reorganization After Stroke in Humans," Stroke, 31:1210-1216 (2000).
Malenka, R.C. and Nicoll, R.A., "Long-Term Potenetiation—A Decade of Progress?," Neuroscience, vol. 285, No. 5435, Issue of Sep. 17, 1999, pp. 1870-1874.
Martinez et al., "Motor hand recovery after stroke Prognostic yield of early transcranial magnetic stimulation," Electromyography. Clin. Neurophysiology, vol. 39, pp. 405-410 (1999).
Netz et al., "Reorganization of motor output in the non-affected hemisphere after stroke," Brain, 120, pp. 1579-1586 (1997).
Nitsche, M.A. and Paulus, W., "Excitability changes induced in the human motor cortex by weak transcranial direct current stimulation," The Journal of Physiology, vol. 527.3, pp. 663-639 (2000).
Oliveri et al., "Paired transcranial magnetic stimulation protocols reveal a pattern of inhibition and facilitation in the human parietal cortex," The Journal of Physiology, 529.2, pp. 461-468 (2000).
Pascual-Leone et al., "Study and Modulation of Human Cortical Excitability With Transcranial Magnetic Stimulation," Journal of Clinical Neurophysiology, vol. 15, No. 4 (1998).
Pascual-Leone et al., "Transcranial magnetic stimulation and neuroplasticity," Neurophycologia 37, pp. 207-217 (1999).
Rezai, "Neurostimulation," Neurological Research, vol. 22, No. 3 pp. 235-273 (Apr. 2000).
Rossi et al., "Effects of Repetitive Transcranial Magnetic Stimulation on Movement-related Cortical Activity in Humans," Cerebral Cortex, vol. 10, No. 8, pp. 802-808 (Aug. 2000).
Roux et al., "Chronic Motor Cortex Stimulation for Phantom Limb Pain: A Functional Magnetic Resonance Imagining Study: Technical Cast Report," Neurosurgery, vol. 49, No. 3 (Mar. 2001).

Saitou et al., "Cerebral Blood Volume and Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).

Sandkuhler, "Learning and memory in pain pathways," Pain 88, pp. 113-118 (2000).

Sanes, "The Relation between Human Brain Activity and Hand Movements," NeuroImage 11, pp. 370-374 (2000).

Sanes, J.N. and Donoghue, J.P., "Plasticity and Primary Motor Cortex," Annu. Rev. Neurosci. 23:393-415 (2000).

Schiff et al., "A neuromodulation strategy for rational therapy of complex brain injury states," Neurological Research, vol. 22 pp. 267-272 (Apr. 2000).

Shimizu et al., "Therapeutic efficacy of transcranial magnetic stimulation for hereditary spinocerebellar degeneration," Tohoku Journal of Experimental Medicine, 189(3):203-11 (Nov. 1999).

Siebner et al., "Lasting cortical activation after repetitive TMS of the motor cortex," Neurology 54, pp. 956-963 (Feb. 2000).

Stefan et al., "Introduction of plasticity in the human motor cortex by paired associative stimulation," Brian, vol. 123, No. 3, pp. 575-584 (Mar. 2000).

Turton et al., "Contralateral and ipsilateral EMG responses to transcranial magnetic stimulation during recovery of arm and hand function after stroke," Electroencephalography and Clinical Neurophysiology 101 pp. 316-328 (1996).

Turton, A. and Lemon, R.N., "The contribution of fast corticospinal input to the voluntary activation of proximal muscles in normal subjects and in stroke patients," Exp. Brain Res., vol. 129, pp. 559-572 (1999).

Van Der Lee et al., "The Intra- and Interrater Reliability of the Action Research Arm Test: A Practical Test of Upper Extremity Function in Patients With Stroke," Arch. Phys. Med. Rehabil., vol. 82 pp. 14-19 (Jan. 2001).

Walker-Batson et al., "Amphetamine Paired With Physical Therapy Accelerates Motor Recovery After Stroke," Stroke, vol. 26, No. 12, pp. 2254-2259 (1995).

Ziemann et al., "Modulation of Plasticity in Human Motor Cortex after Forearm Ischemic Nerve Block," The Journal of Neuroscience 18(3):1115-1123 (Feb. 1998).

Ziemann et al., "Modulation of Plasticity in Human Motor Cortex after Forearm Ischemic Nerve Block," The Journal of Neuroscience, vol. 18, No. 3, pp. 1115-1123 (Feb. 1998).

Barr, Deborah et al., "Induction and Reversal of Long-Term Potentiation by Low-and High-Intensity Theta Pattern Stimulation," The Journal of Neuroscience, 15(7): pp. 5402-5410 (Jul. 1995).

Barres et al., "Proliferation of oligodendrocyte precursor cells depends on electrical activity in axons," Nature; Medical Research Council Developmental Neurobiology Programme, Department of Biology, University College, London, p. 258-260, (Jan. 21, 1993).

Behrens, T. et al., "Non-invasive mapping of connections between human thalamus and cortex using diffusion imaging," Nature neuroscience, vol. 6 No. 7, pp. 750-757 (Jul. 2003).

Beveridge, J. A., "Use of Exogenous Electric Current in the Treatment of Delayed Lesions in Peripheral Nerves," Plastic and Reconstructive Surgery, Oct. 1988, vol. 82, No. 4, pp. 573-579.

Bezard et al., "Cortical Stimulation and Epileptic Seizure: A Study of the Potential Risk in Primates," Neurosurgery, vol. 45, No. 2, Aug. 1999, 346-350.

Bluestone, Avraham Y. et al., "Three-dimensional optical tomography of hemodynamics in the human head," Optics Express, vol. 9, No. 6, pp. 272-286 (Sep. 10, 2001).

Brain Electrical Stimulation to Enhance Recovery After Stroke, ClinicalTrials.gov, URL: http://www.clinicaltrials.gov/ct/show/NCT00085657?order=2 [Retrieved on Dec. 22, 2005].

Burnett, Mark G. et al., "Diffuse optical measurement of blood flow, blood oxygenation, and metabolism in a human brain during sensorimotor cortex activation," Optics Letters, vol. 29, No. 15, pp. 1766-1768 (Aug. 1, 2004).

Bury, Scott et al., "The Effects of Behavioral Demand on Motor Cortical and Cerebellar Structural Plasticity After Brain Injury in Adult Rats," http://www.mcmaster.ca-inabis98-schallert-bury0827-two.html#introduction, 2 pages [Retrieved on Mar. 1, 2003].

Cheun et al., "Differentiation of a Stem Cell Line Toward a Neuronal Phenotype," Int. J. Devl. Neuroscience, vol. 9, No. 4, pp. 391-404 (1991).

Cicinelli et al., "Transcranial magnetic stimulation reveals an interhemispheric asymmetry of cortical inhibition in focal epilepsy," Neurophysiology, vol. 11, No. 4 Mar. 20, 2000, pp. 701-707.

Cincotta et al., "Suprathreshold 0.3 Hz repetitive TMS prolongs the cortical silent period: potential implications for therapeutic trials in epilepsy," Clinical Neurophysiology, vol. 114, 2003, pp. 1827-1833, Elsevier Ireland Ltd.

CNN.com, Health, "Lab Zaps Strokes with Magnetic Pulses," http://www.cnn.com/2004/HEALTH/conditions/11/29/zapping.strokes.ap/, Nov. 29, 2004, 4 pages [Retrieved on Dec. 2, 2004].

Cramer et al., "Use of Functional MRI to Guide Decisions in a clinical Stroke Trial," Stroke, Journal of the American Heart Association, May 2005, pp. e50-e52, American Heart Association, Dallas TX.

Cytokines Web Clinical Significance, Cytokines Web, 2 pages, URL: http:—cmbi.bjmu.edu.cn-cmbidata-cgf-CGF_Database-cytweb-roles-index.html [Retrieved on Sep. 2, 2005].

De Ridder, Dirk et al., "Magnetic and electrical stimulation of the auditory cortex for intractable tinnitus," Journal Neurosurg., vol. 100, pp. 560-564, (Mar. 2004).

Di Lazzaro, V. et al., "Theta-burst repetitive transcranial magnetic stimulation suppresses specific excitatory circuits in the human motor cortex," Physiology in Press; published online on Apr. 21, 2005 as 10.1113-jphysiol.2005.087288.

Ding, Yuemin et al., "Neural Plasticity After Spinal Cord Injury," Current Pharmaceutical Design vol. 11, No. 11, pp. 1441-1450, Abstract Only, 1 page (Apr. 2005).

Duncan, Pamela W. et al., "Defining post-stroke recovery: implications for design and interpretation of drug trials," Neuropharmacology vol. 39, pp. 835-841 (2000).

Ferrari, A. et al., "Immature human NT2 cells grafted into mouse brain differentiate into neuronal and glial cell types," FEBS Letters, Dec. 8, 2000, pp. 121-125, vol. 486, No. 2, Elsevier Science B.V., Amsterdam.

Fregni et al., "Antiepileptic Effects of Repetitive Transcranial Magnetic Stimulation in Patients with Cortical Malformations: An EEG and Clinical Study," ASSFN Proceedings 2004, Stereotactic and Functional Neurosurgery, 2005, 83:57-62.

Fregni, Felipe et al., "Anodal Transcranial Direct Current Stimulation of Prefrontal Cortex Enhances Working Memory," Experimental Brain Research vol. 166, No. 1, pp. 23-30 (Sep. 2005).

Hagemann, Georg et al., "Increased Long-Term Potentiation in the Surround of Experimentally Induced Focal Cortical Infarction," Annals of Neurology, vol. 44, No. 2, pp. 255-258 (Aug. 1998).

Haglund, Michael M. et al., "Optical imaging of epileptiform and functional activity in human cerebral cortex," Nature, Aug. 20, 1992, pp. 668-671, vol. 358, Nature Publishing Group.

Hayakawa, Toshiji et al., "Changes in Cerebral Oxygenation and Hemodynamics During Obstructive Sleep Apneas," Chest, vol. 109, pp. 916-921 (1996).

Hoshi, Yoko et al., "Detection of dynamic changes in cerebral oxygenation coupled to neuronal function during mental work in a man," Neuroscience Letters, vol. 150, pp. 5-8 (1993).

Hoshino et al., "Application of multichannel near-infrared spectroscopic topography to physiological monitoring of the cortex during cortical mapping: technical case report," Surgical Neurology, vol. 64, pp. 272-275 (2005).

How Imagent™ Works. ISS Inc., http://www.iss.com-Products-imagent_fmri.html, 1 page [Retrieved on Oct. 14, 2005].

Huang, Ying-Zu et al., "Theta Burst Stimulation of the Human Motor Cortex," Neuron, vol. 45, pp. 201-206 (Jan. 20, 2005).

Hummel, Friedhelm et al., "Effects of non-invasive cortical stimulation on skilled motor function in chronic stroke," Brain Advance Access, pp. 1-10, (Jan. 5, 2005).

Imagent™ Functional Brain Imaging System, ISS, Inc., http://www.iss.com-Products-imagent.html, 2 pages [Retrieved on Oct. 14, 2005].

Imagent™ functional Near Infrared Imaging System (fNIRS) Brain Imaging Using Infrared Photons, ISS Inc., http://www.iss.com-products-imagent-Imagent.pdf, 8 pages [Retrieved on Oct. 14, 2005].

Ishibashi, Tomoko et al., "Astrocytes Promote Myelination in Response to Electrical Impulses," Neuron 49, pp. 823-832, (Mar. 16, 2006).

Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp. 571-577 (Dec. 2003).

Kelly-Spratt, K. "Transfection of PC-12 cells: a model system for primary neuronal cells," Qiagen News, Customer application article, www.qiagen.com, Issue 4, 1998, 2 pages.

Keyvani, Kathy et al., "Suppression of proteasome C2 contralateral to ischemic lesions in rat brain," Brain Research, vol. 858, pp. 386-392, 2000.

Kilgard, Michael et al., "Cortical Map Reorganization Enabled by Nucleus Basalis Activity," Science, vol. 279 pp. 1714-1717 (Mar. 13, 1998).

Kimura, K. et al., "Electrically induced neurite outgrowth of PC12 cells on the electrode surface," Entrez PubMed, http://www.ncbi.nlm.nih.gov/entrez/query.fcgi?db=pubmed&cmd=Retrieve &dopt=Abstract, 1 page.

Kinoshita et al., "Electric cortical stimulation suppresses epileptic and background activities in neocortical epilepsy and mesial temporal lobe epilepsy," Clinical Neurophysiology, vol. 116, 2005, pp. 1291-1299, Elsevier Ireland Ltd.

Kossoff et al., "Effect of an External Responsive Neurostimulator on Seizures and Electrographic Discharges during Subdural Electrode Monitoring," Epilepsia 45(12):1560-1567, 2004, Blackwell Publishing, Inc.

Lang, Nicolas et al., "Preconditioning with Transcranial Direct Current Stimulation Sensitizes the Motor Cortex to Rapid-Rate Transcranial Magnetic Stimulation and Controls the Direction of After-Effects," Biol Psychiatry 2004:56:634-639, 2004 Society of Biological Psychiatry.

Larson, John et al., "Reversal of LTP by theta frequency stimulation," Brain Research, 600: pp. 97-102 (1993).

Lazar, M. et al., "White Matter Tractography Using Diffusion Tensor Deflection," Huamn Brain Mapping, 18:306-321, (2003).

L-Dopa dyskinesias, BioChemistry of PD, http://www.mayo.edu-fdp-pd-info-dyskinesias.htm [Retrieved on Dec. 22, 2005].

Lutsep et al., "Safety of Cortical Stimulation in Patients with Hemiparetic Stroke," Oasis, Online Abstract Submission and Invitation System—Program Planner, International Stroke Conference 2005, 1 pages, American Stroke Association.

Mansur, C.G. et al., "A sham stimulation-controlled trial of rTMS of the unaffected hemisphere in stroke patients," Neurology, vol. 64, pp. 1802-1804 (2005).

Martin et al., "Transcranial Magnetic Stimulation as a Complementary Treatment for Aphasia," Semin Speech Language, vol. 25, pp. 181-191 (2004) Abstract Only- 1 page.

Mendonca, A.C., "Directly applied low intensity direct electric current enhances peripheral nerve regeneration in rats," Journal of Neuroscience Methods, 2003, vol. 129, pp. 183-190.

Meyerson, B.A. et al., "Motor Cortex Stimulation as Treatment of Trigeminal Neuropathic Pain", Acta Neurochirurgica Supplementum, vol. 58, pp. 150-153 (1993).

Misawa et al., "Low-frequency transcranial magnetic stimulation for epilepsia partialis continua due to cortical dysplasia," Journal of the Neurological Sciences, vol. 234, 2005, pp. 37-39.

Montgomery, "Thalamic Stimulation," Neuroscience Pathways, The Cleveland Clinic Foundation, 2 pages.

Motamedi et al., "Optimizing Parameters for Terminating Cortical Afterdischarges with Pulse Stimulation," Epilepsia 43(8):836-846, 2002, Blackwell Publishing, Inc.

Nitsche, Michael A. et al. "Facilitation of Implicit Motor Learning by Weak Transcranial Direct Current Stimulation of the Primary Motor Cortex in the Human," Journal of Cognitive Neuroscience 15:4, pp. 619-626, 2003 Massachusetts Institute of Technology.

Nitsche, Michael A. et al., "Level of action of cathodal DC opographyn induced inhibition of the human motor cortex," Dec. 2, 2002, Clinical Neurophysiology 114 (2003) 600-604.

Nudo, Randolph J. et al., "Recovery after damage to motor cortical areas," Current Opinion in Neurobiology, vol. 9, Issue 6, pp. 740-747, Dec. 1, 1999.

Panchanathan, Sethuraman et al., "Rehabilitation of patients with hemispatial neglect using visual-haptic feedack in Virtual reality environment," http://www.public.asu.edu-~tmcdani-publications.htm, 5 pages [Retrieved on Dec. 22, 2005].

Paulus, W, "Supplements to Clinical Neurophysiology," Transcranial Magnetic Stimulation and Transcranial Direct Current Stimulation (Supplements to Clinical Neurophysiology; vol. 56), 249-254, 2003 Elsevier Science, B.V.

Paulus, Walter, "Toward Establishing a Therapeutic Window for rTMS by Theta Burst Stimulation," Neuron, vol. 45, pp. 181-183 (Jan. 20, 2005).

Penn, Michael, "Stemming Parkinson's," On Wisconsin Alumni Magazine, Summer 2003, http://www.uwalumni.com-onwisconsin-2003_summer-research.html, 1 page [Retrieved on Dec. 22, 2005].

Politis, M. J., "Mammalian Optic Nerve Regeneration Following the Application of Electric Fields," The Journal of Trauma, Nov. 1988, vol. 28, No. 11, pp. 1548-1552.

Price, J. et al., "Neurotransplantation in neurodegenerative disease: a survey of relevant issues in developmental neurobiology," Novartis Foundation Symposium 231, 2000, pp. 148-165, Wiley, Chichester, UK.

Robinson, Kenneth R., "The Responses of Cells to Electrical Fields: A Review," The Journal of Cell Biology, vol. 101, pp. 2023-2027 (Dec. 1985).

Schaefer, Pamela W. et al., "Assessing Tissue Viability with MR Diffusion and Perfusion Imaging," AJNR, 24: pp. 436-443 (Mar. 2003).

Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).

Schulz et al., "Localization of Epileptic Auras Induced on Stimulation by Subdural Electrodes," Epilepsia, Dec. 1997, vol. 38, Issue 12, pp. 1321-1329.

SCIRun, Scientific Computing and Imaging Institute. http://www.sofware.sci.utah.edu-scirun.html, 2 pages [Retrieved on Jul. 24, 2005].

Sioutos et al. Continuous Regional Cerebral Cortical Blood Flow Monitoring in Head-injured Patients, Neurosurgery, vol. 36, No. 5, May 1995, pp. 943-949.

Storer et al., "Microiontophoretic application of serotonin (5HT)1B/1D agonists inhibits trigeminal cell firing in the cat," Brain, 1997, vol. 120, Issue 12, pp. 2171-2177, Oxford University Press.

Strangman, Gary et al., "A Quantitative Comparison of Simultaneous BOLD fMRI and NIRS Recordings during Functional Brain Activation," NeuroImage, vol. 17, pp. 719-731 (2002).

Strangman, Gary et al., "Factors affecting the accuracy of near-infrared spectroscopy concentration calculations for focal changes in oxygenation parameters," NeuroImage, vol. 18, pp. 865-879 (2003).

Strangman, Gary et al., "Non-Invasive Neuroimaging Using Near-Infrared Light," Biological Psychiatry, vol. 52, pp. 679-693 (2002).

Strens, Lucy et al., "The Ipsilateral Human Motor Cortex Can Functionally Compensate for Acute Contralateral Motor Cortex Dysfunction," Current Biology, vol. 13, pp. 1201-1205 (Jul. 15, 2003).

Suzuki et al., "Selective Electrical Stimulation of Postganglionic Cerebrovascular Parasympathetic Nerve Fibers Originating from the Sphenopalatine Ganglion Enhances Cortical Blood Flow in the Rat," Journal of Cerebral Blood Flow and Metabolism, May 1990, 10(3):383-91.

Taga, Gentaro et al., "Brain imaging in awake infants by near-infrared optical topogrpahy," PNAS, vol. 100, No. 19, pp. 10722-10727 (Sep. 16, 2003).

Tang, Cha-Min et al., "Optical Coherence Tomography of the Human Basal Ganglion," Deep Brain Stimulation Consortium Meeting Program Book, Sep. 29-30, 2003, Washington DC.

The GES 250 for Dense-Array EEG Research, Electrical Geodesics, Inc., http://www.egi.com/ges250r_n.html, 3 pages [Retrieved on Aug. 25, 2005].

The INVOS Cerebral Oximeter, Somanetics, http://www.somanetics.net/invos.htm, 1 page [retrieved from the internet on Dec. 22, 2005].

The National Institutes of Health (NIH) Consensus Development Program, "Surgery for Epilepsy," National Institutes of Health Consensus Development conference Statement, Mar. 19-21, 1990, 16 pages.

Theoret, Hugo et al., "Exploring Paradoxical Functional Facilitation with TMS," Supplements to Clinical Neurophysiology, vol. 56, pp. 211-219 (2003).

Thomas, Carmen et al., "Do Children with aggressive behavior have temporal lobe changes?" Alasbimn Journal, Year 5, No. 19, 8 pages (Jan. 2003).

Timmermann, Lars et al., "The cerebral oscillatory network of parkinsonian resting tremor," Brain, vol. 126, pp. 199-212, (2003).

Toronov, Vlad et al., "Near-infrared study of fluctuations in cerebral hemodynamics during rest and motor stimulation: Temporal analysis and spatial mapping," Medical Physics, vol. 27, No. 4, pp. 801-815 (Apr. 2000).

Tractrography, Absolute Astronomy Reference, http://www.absoluteastronomy.com-encyclopedia-T-Tr-Tractography.htm, 2 pages [Retrieved on Jul. 24, 2005].

Tsubokawa, T. et al., "Chronic Motor Cortex Stimulation for the Treatment of Central Pain," Acta Neurochirurgica, Supplementum. vol. 52, pp. 137-139 (1991).

Tsubokawa, T. et al., "Chronic Motor Cortex Stimulation in Patients with Thalamic Pain," J. Neurosurg 78:393-401, (Mar. 1993).

Tsubokawa, T. et al., "Treatment of Thalamic Pain by Chronic Motor Cortex Stimulation", Pace, vol. 14, pp. 131-134 (Jan. 1991).

Tuch, D. et al., "Conductivity Tensor Mapping of the Human Brain Using Diffusion Tensor MRI," Neurobiology, vol. 98 No. 20, pp. 11697-11701 (Sep. 25, 2001).

Vanderkooy et al., "Resolution Below the Least Significant Bit in Digital Systems with Dither," JAES, Mar. 1984, vol. 32, No. 3, pp. 106-113.

Velasco et al. "Absolute and Relative Predictor Values of Some Non-Invasive and Invasive Studies for the Outcome of Anterior Temporal Lobectormy," Science Direct, vol. 31, Issue 1, Jan.-Feb. 2000, pp. 62-74, Elsevier Science, Inc.

Velasco et al., "Acute and Chronic Electrical Stimulation of the Centromedian Thalamic Nucleus: Modulation of Reticulo-Cortical Systems and Predictor Factors for Generalized Seizure Control," Archives of Medical Research, vol. 31, 2000, pp. 304-315, Elsevier Science, Inc.

Velasco et al., "Electrical Stimulation for Epilepsy: Stimulation of Hippocampal Foci," Stereotactic and Functional Neurosurgery, vol. 77, 2001, pp. 223-227.

Velasco et al., "Subacute and Chronic Electrical Stimulation of the Hippocampus on Intractable Temporal Lobe Seizures: Preliminary Report," Archives of Medical Research, vol. 31, 2000, pp. 316-328, Elsevier Science, Inc.

Velasco et al., "Subacute Electrical Stimulation of the Hippocampus Blocks Intractable Temporal Lobe Seizures and Paroxysmal EEG Activities," Epilepsia, vol. 41, No. 2, 2000, pp. 158-169, Lippincott Williams & Wilkins, Philadelphia.

Waxman et al., "The Interictal Behavior Syndrome of Temporal Lobe Epilepsy," Arch Gen Psychiatry, vol. 32, Dec. 1975, pp. 1580-1586.

Weinand et al., "Cerebral blood flow and temporal lobe epileptogenicity," J Neurosurg, vol. 86, Feb. 1997, pp. 226-232.

Weinand et al., "Cerebral blood flow and temporal lobe epileptogenicity," Neurosurgical Focus, Nov. 1996, vol. 1, No. 5, AANS.ORG, http://www.aans.org/education/journal/neurosurgical/nov96/1-5-3.asp, 17 pages.

Weinand et al., Long-term ictal monitoring with subdural strip electrodes: prognostic factors for selecting temporal lobectomy candidates, J Neurosurg, vol. 77, 1992, pp. 20-28.

Weinand et al., "Surface cortical cerebral blood flow monitoring and single photon emission computed tomography: prognostic factors for selecting temportal lobectomy candidates," Seizure, vol. 3, 1994, pp. 55-59.

Weinand et al., "Targeted Subthreshold Cortical Stimulation for Recovery of Motor Hand Function following Hemiparetic Stroke," Abstract:Apr. 18, 2005, AANS.org, http://www.aans.org/Library/Article.aspx?ArticleId=24934, 2 pages.

Weinand, Martin E. et al., "Cerebral blood flow and temporal lobe epileptogenicity," Retrieved from the Internet on Dec. 22, 2005, http://www.aans.org/education/journal/neurosurgical/nov96/1-5-3.asp, 13 pages.

Woodbury, D. et al., "Adult Rat and Human Bone Marrow Stromal Cells Differentiate Into Neurons," Journal of Neuroscience Research, 2000, vol. 61, pp. 364-370, Wiley Interscience, New York, NY.

Yamamoto et al., "Low-frequency Electric Cortical Stimulation Has an Inhibitory Effect on Epileptic Focus in Mesial Temporal Lobe Epilepsy," Epilepsia, vol. 43, No. 5, 2002, pp. 291-295, Blackwell Publishing, Inc.

Yokoh, Arika et al., "Intermittent versus continuous brain retraction," Journal of Neurosurgery, vol. 58, pp. 918-923 (Jun. 1983).

\* cited by examiner

METHODS FOR TREATING AND/OR COLLECTING INFORMATION REGARDING NEUROLOGICAL DISORDERS, INCLUDING LANGUAGE DISORDERS

CROSS-REFERENCE TO RELATED APPLICATIONS

The present application relates to and claims priority to pending U.S. Provisional Application No. 60/432,073, entitled "System and Method for Treating Parkinson's Disease and Other Movement Disorders," filed Dec. 9, 2002, and pending U.S. Provisional Application No. 60/515,309, entitled "Methods for Treating and/or Collecting Information Regarding Neurological Disorders, Including Language Disorders," filed Oct. 28, 2003, both incorporated herein by reference. The present application also relates to pending U.S. application Ser. No. 10/072,700, filed Feb. 7, 2002, and incorporated herein by reference.

TECHNICAL FIELD

The present invention is directed toward methods for treating and/or collecting information regarding neurological disorders, including language disorders, for example, aphasias.

BACKGROUND

A wide variety of mental and physical processes are controlled or influenced by neural activity in particular regions of the brain. For example, various physical or cognitive functions are directed or affected by neural activity within the various regions of the cerebral cortex. For most individuals, particular areas of the brain appear to have distinct functions. In the majority of people, for example, the areas of the occipital lobes relate to vision; the regions of the left inferior frontal lobes relate to language; portions of the cerebral cortex appear to be involved with conscious awareness, memory, and intellect; and particular regions of the cerebral cortex as well as the basal ganglia, the thalamus, and the motor cortex cooperatively interact to facilitate motor function control.

Aphasias are neurological disorders that affect the language centers of the brain. Aphasias are typically caused by brain lesions that result from a stroke or head injury. Different aphasias result from damage to different portions of the brain's language centers. For example, Broca's aphasia typically results from a large frontal lobe lesion and causes the patient to speak with great effort in a nonfluent manner, while generally not affecting the patient's comprehension of single words and simple sentences. Wernicke's aphasia typically results from damage to the left temporal lobe of the brain and impacts the patient's comprehension of words and sentences, usually without affecting the patient's fluency. Global aphasia can affect both Broca's area and Wernicke's area of the brain and can accordingly adversely affect both the patient's comprehension and speech fluency. Conduction aphasia is caused by damage to structures that interact with the major language areas of the brain. Conduction aphasia does not have as substantial an effect on the patient's comprehension or fluency as do other aphasias, but reduces the patient's ability to repeat sentences verbatim or easily name pictures and objects.

Practitioners have developed imaging techniques to isolate the portions of the brain affected by various aphasias. For example, Perani, et al. disclose identifying and tracking neurological functioning connected with language-based activities by obtaining functional magnetic resonance imaging (fMRI) data while the patient executes language-based tasks (see "A fMRI Study of Word Retrieval in Aphasia," Brain and Language 85 (2003) pp. 357-368). Practitioners have also treated aphasia, for example, with conventional and/or melodic speech therapies, with drugs (e.g., amphetamines and other neuro-stimulatory agents) and with transcutaneous magnetic stimulation (TMS) applied to the brain. However, these techniques all suffer from drawbacks. In particular, the efficacies of speech therapy and drug-based techniques have not been conclusively demonstrated, and the effects of TMS are short-lived.

DETAILED DESCRIPTION

The following disclosure describes several methods for collecting information regarding neurological disorders, including language disorders, and methods for treating such disorders using electrical stimulation, for example, cortical stimulation. Cortical stimulation has been applied in other contexts, for example to enhance the recovery of cortical functions after a brain injury affecting motor capabilities. Several features of methods in accordance with embodiments of the invention are set forth and described in FIGS. 1A-10. It will be appreciated that methods in accordance with other embodiments of the invention can include additional procedures or features different than those shown in FIGS. 1A-10.

Additionally, methods in accordance with several embodiments of the invention may not include all of the features shown in these Figures.

Figure 1A:
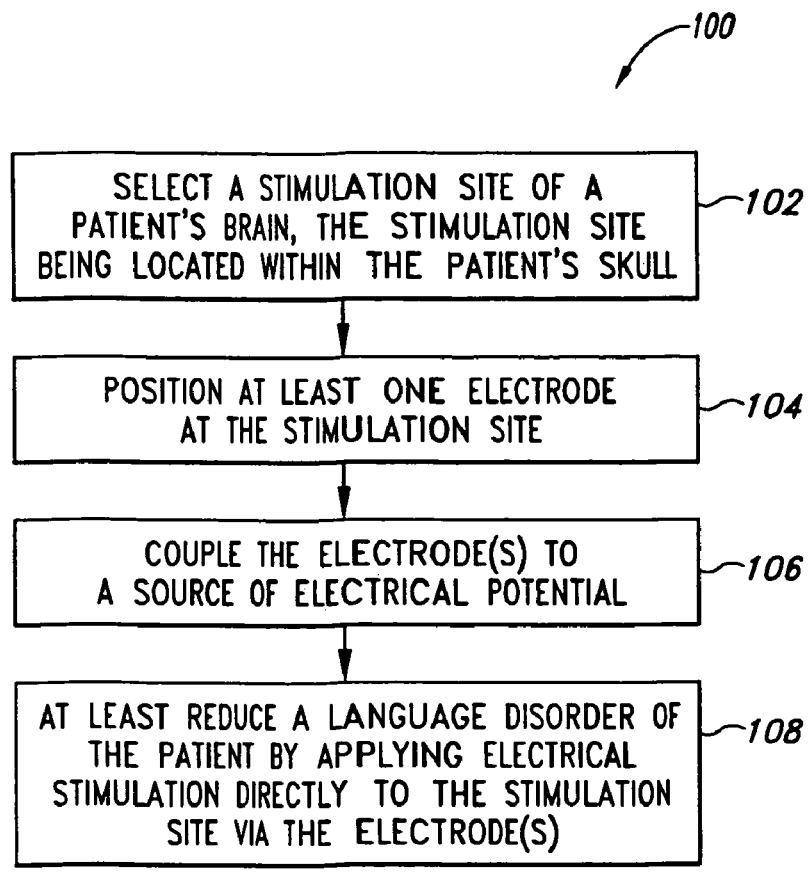
FIG. 1A is a flow chart illustrating a method for treating a language disorder in accordance with an embodiment of the invention.

FIG. 1A is a flow chart illustrating a method 100 for treating language disorders in accordance with an embodiment of the invention. In one aspect of this embodiment, the method 100 includes selecting a brain stimulation site located within the patient's skull (method portion 102). At least one electrode can then be positioned at the stimulation site (method portion 104). The method 100 can further include coupling the electrode(s) to a source of electrical potential (method portion 106) and at least reducing a language disorder of the patient by applying electrical stimulation directly to the stimulation site via the electrode(s) (method portion 108).

In one particular aspect of this embodiment, the patient's language disorder can be entirely eliminated. In another particular aspect of this embodiment, the effects of the disorder can at least be diminished. In a further aspect of either embodiment, the stimulation site can be selected to be on the left side of the patient's brain, e.g., at or proximate to the language centers of the brain. In another aspect of these embodiments, the homologous structures on the right side of the patient's brain can be stimulated in addition to or in lieu of stimulating the left side of the patient's brain. Further details of the areas of the brain selected for stimulation, and the devices that apply the stimulation are discussed later with reference to FIGS. 2-10.

Figure 1B:
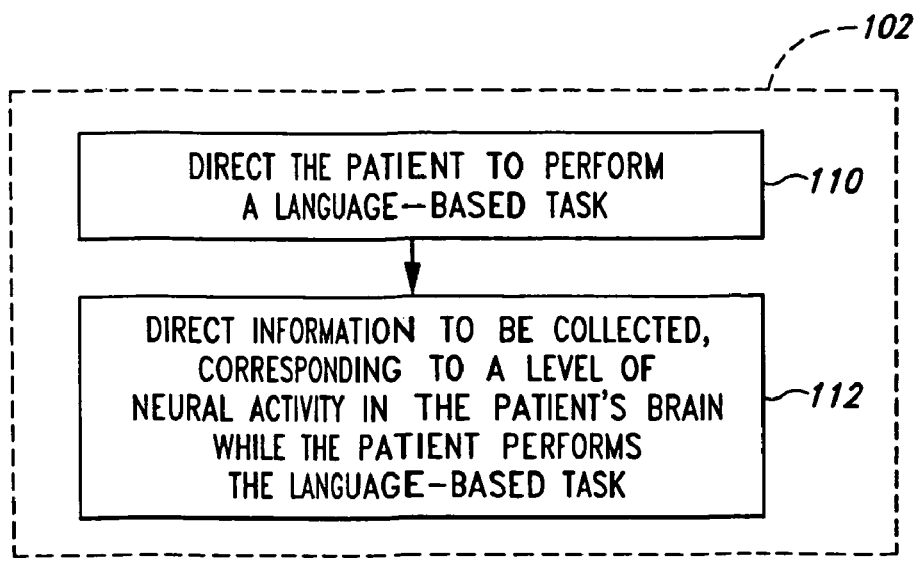
FIG. 1B is a flow chart illustrating details of a method for selecting a stimulation site used for treating language disorders in accordance with another embodiment of the invention.

Referring next to FIG. 1B, the process of selecting a stimulation site (process portion 102) can include directing the patient to perform a language-based task (process portion 110). The method can further include directing information to be collected while the patient performs the language-based task, with the information corresponding to a level of neural activity in the patient's brain while the task is performed (process portion 112). In one embodiment, the foregoing process portions can be completed while the patient is under the influence of an amphetamine or other neuroexcitatory drug, and in other embodiments, such agents are not present in the patient's body during the procedure.

In one embodiment, process portion 112 can be carried out at least in part by a human operator, for example, a technician or physician who operates an imaging system. In another embodiment, the process of directing the collection of information can be performed partially or entirely by a computer, for example, by a hardware- and/or software-based routine that collects the information corresponding to the level of neural activity. In either embodiment, the information can take several forms and/or can correspond to the level of neural activity in the patient's brain by virtue of any of several techniques, as described below. As is also described below, a practitioner can direct the patient to perform one or more of a variety of language-based tasks that generate a neural response corresponding to the collected information.

In a particular aspect of an embodiment of the invention, the language-based task performed by the patient does not require the patient to actually vocalize. Instead, the patient can be directed to merely think of a word, letter, phrase or other language component. For example, the patient can be directed to silently generate a verb associated with a common noun, silently repeat a noun, silently retrieve a word based on a letter cue, or silently retrieve a word based on a visual cue. In particular cases, the patient can be directed to think of words beginning with the letter "C," for example, or can be shown a picture of a cat and asked to think of the word represented by the picture. The patient can also be asked to respond nonverbally to an oral task that requires the patient to understand the difference between two auditory commands.

In any of these embodiments, the patient need not use motor neurons to execute the selected task. An advantage of this arrangement is that reducing the number of motor neurons active while the patient performs the selected task can more clearly highlight those areas of the brain associated purely with the cognitive aspect of the language-based task. Put another way, this technique can reduce or eliminate the recorded activity of motor neurons, which might otherwise clutter or obscure the cognitive, language-based information of interest.

In other embodiments, the patient can be directed to perform any of the above tasks verbally. The practitioner can direct the patient to perform a verbal task when, for example, the motor activity associated with speech production will clearly not obscure neural responses associated with non-motor aspects of language-based tasks, and/or when it is desirable to locate and/or stimulate regions of the brain associated with motor aspects of the language-based tasks. In still further embodiments, the patient can be directed to perform a variety of language-based tasks and the information collected while the patient performs each task can be combined to aid the practitioner in determining a stimulation site. This technique can be used to identify multiple stimulation sites and/or to more definitively or precisely locate a particular stimulation site. In any of these embodiments, the methods described above include collecting information, such as imaging information, while the patient performs the task, as described in greater detail below.

The collected information can take the form of an image, generated using functional magnetic resonance imaging (fMRI) techniques, magnetic resonance imaging (MRI) techniques, computed tomography (CT) techniques, single photon emission computed tomography (SPECT) techniques, positron emission tomography (PET) techniques and/or other techniques. In any of these embodiments, a practitioner can view the image and, based at least in part on the image, identify a stimulation site for treating the language disorder. For example, the images can be color-coded or can have other distinguishing characteristics that allow the practitioner to distinguish active regions from inactive regions. In a particular embodiment, the active regions can be identified by a relatively elevated blood oxygen level, and in other embodiments, these regions can be identified on the basis of other characteristics.

In other embodiments, the foregoing techniques can be used to generate a digital representation of brain activity without necessarily generating a visible image. In a particular aspect of these embodiments, an algorithm or other computer-based method can be used to determine the stimulation site, based upon the digital representation described above. Whether or not the collected information is in the form of a visually accessible image, it can aid the practitioner in determining where to implant electrodes for applying electrical stimulation. The locations for the electrodes and the techniques for placing the electrodes at the stimulation sites are described in greater detail below with reference to FIGS. 2-9.

Methods in accordance with still further embodiments of the invention can include subsets of the method portions shown in FIGS. 1A-1B. For example, a method in accordance with one embodiment of the invention includes directing the patient to perform a language-based task and then directing information to be collected, with the information corresponding to a level of neural activity in the patient's brain while the patient performs the language-based task. The method can further include selecting a stimulation site based at least in part on the information. The stimulation site can be located within the patient's skull and can receive an electrode coupleable to an electrical current.

Figure 2:
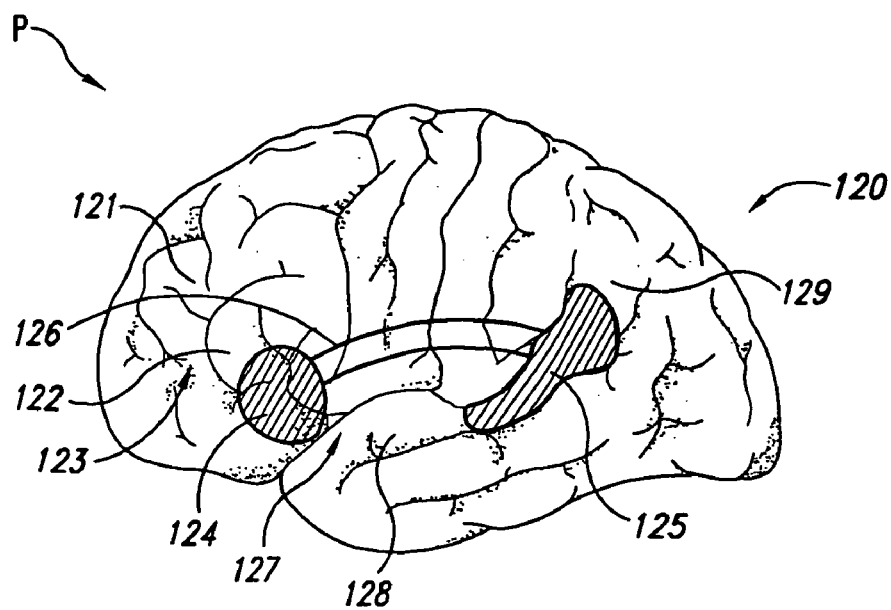
FIG. 2 is a partially schematic, isometric illustration of a human brain illustrating areas associated with language comprehension and production and suitable for stimulation in accordance with embodiments of the invention.

FIG. 2 is an isometric, left side view of the brain 120 of a patient P. As described above, certain sectors of the brain 120 are typically responsible for language-based tasks. These sectors can be identified using the techniques described above, and can be selected as stimulation sites. Accordingly, the sectors can be targeted to receive direct electrical stimulation for reducing and/or eliminating the effects of a language disorder.

In one embodiment, the targeted areas of the brain 120 can include Broca's area 124 and/or Wernicke's area 125. In other embodiments, sections of the brain 120 anterior to, posterior to, or between these areas can be targeted in addition to or in lieu of targeting Broca's area 124 and Wernicke's area 125. For example, the targeted areas can include the middle frontal gyrus 121, the inferior frontal gyrus 122 and/or the inferior frontal lobe 123 anterior to Broca's area 124. In other embodiments, the areas targeted for stimulation can include the superior temporal lobe 127, the superior temporal gyrus 128, and/or the association fibers of the arcuate fasciculus 126. In still further embodiments, the targeted areas can include the inferior parietal lobe 129 and/or other structures, including the supramarginal gyrus, angular gyrus, retrosplenial cortex and/or the retrosplenial cuneus of the brain 120.

Figure 3:
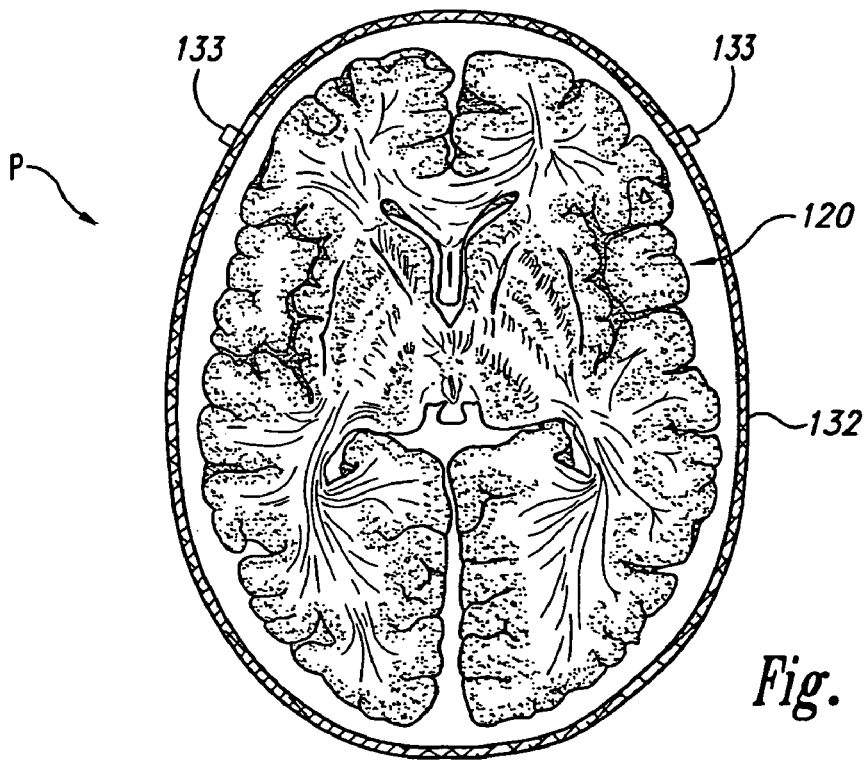
FIG. 3 is a partially schematic generally horizontal section through a human brain illustrating reference features suitable for locating stimulation sites in accordance with other embodiments of the invention.

FIG. 3 is a partially schematic, approximately horizontal section through the brain 120 described above with reference to FIG. 2. The stimulation sites described above with reference to FIG. 2 can be identified with reference to anatomical features of the patient, for example, the patient's nose. In other embodiments, the stimulation site can be identified with reference to fiducials 133 positioned in the patient's skull 132. Accordingly, the location of the fiducials 133 can appear on the image (or other display format) used to present the neural activity information and identify the corresponding stimulation sites.

Figure 4:
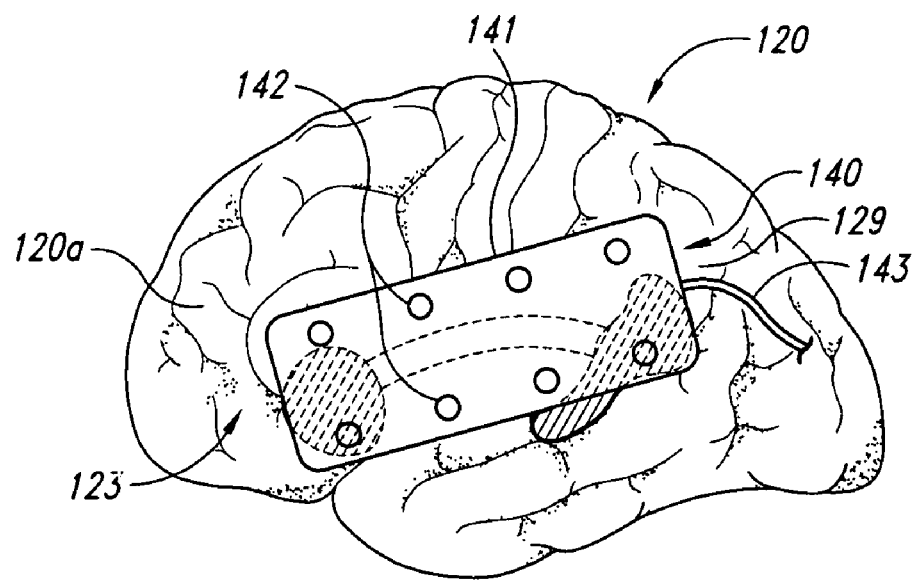
FIG. 4 is a partially schematic, isometric illustration of a human brain having an electrode assembly positioned for stimulation in accordance with an embodiment of the invention.

FIG. 4 is an isometric illustration of the left side 120a of the brain 120 with an electrode assembly 140 positioned to provide stimulation in accordance with an embodiment to the invention. In one aspect of this embodiment, the electrode assembly 140 includes a support 141 carrying a plurality of electrodes 142 (eight are shown in FIG. 4). In a further aspect of this embodiment, the electrode assembly 140 is positioned to cover a plurality of the areas (described above) responsible for carrying out language-based tasks. For example, in one embodiment, the electrode assembly 140 can be sized to extend generally from the inferior frontal lobe 123 to the inferior parietal lobe 129, and can include electrodes 142 located to stimulate any of a plurality of areas between and adjacent to these structures. In any of these embodiments, the electrode assembly 140 can also include a lead 143 coupled to a power supply and/or a pulse system, as described in greater detail below with reference to FIG. 6.

One feature of an embodiment of the electrode assembly 140 described above with reference to FIG. 4 is that it can include an array of electrodes 142 that are spaced apart from each other, for example, along two transverse axes. Accordingly, each electrode 142 can be positioned to stimulate a particular region of the brain 120. An advantage of this arrangement is that a practitioner can stimulate multiple sites of the brain 120 (either simultaneously or sequentially) with a single electrode assembly 140. In one embodiment, the practitioner can stimulate multiple sites of the brain 120 (rather than a single site) to produce enhanced benefits for the patient. In another embodiment, the practitioner can use an electrode assembly 140 having an array of electrodes 142 when it is initially uncertain which area(s) of the patient's brain 120 should be stimulated to produce the most beneficial effect. Accordingly, a practitioner can stimulate a particular area of the brain 120 with one of the electrodes 142, observe the effect on the patient, and if the effect is not the desired effect, stimulate another area of the brain 120 with another of the electrodes 142 and observe the resulting effect, all with a single, implanted assembly 140. In still another embodiment, the practitioner can apply stimulation to different sites for different lengths of time, and/or the practitioner can independently vary other stimulation parameters applied to the electrodes 142. In any of these embodiments, the signal applied to the electrodes 142 can be varied randomly or pseudo-randomly. Further details of the signals applied to the electrodes 142 are described below with reference to FIG. 6.

Figure 5:
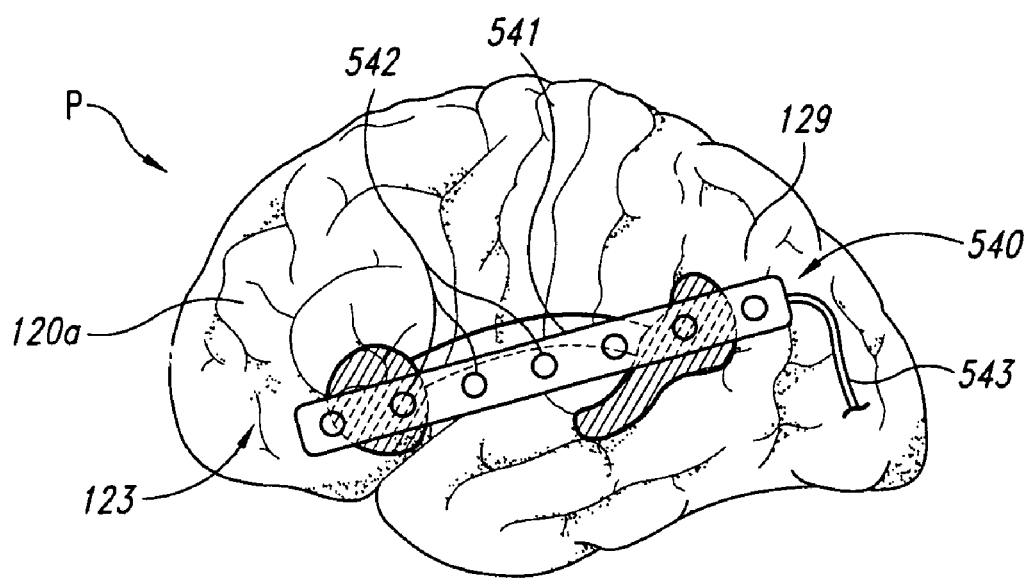
FIG. 5 is a partially schematic, isometric illustration of a human brain and an electrode assembly configured in accordance with another embodiment of the invention.

In another embodiment shown in FIG. 5, the practitioner can implant a generally strip-shaped electrode assembly 540 in the patient P. In one aspect of this embodiment, the electrode assembly 540 can include an elongated support 541 carrying a plurality of linearly aligned electrodes 542 coupled to a lead 543. The electrode assembly 540 can be positioned to extend over a relatively narrow band between the inferior frontal lobe 123 and the inferior parietal lobe 129. In one aspect of this embodiment, the electrode assembly 540 can include six electrodes 542, and in other embodiments, the electrode assembly 540 can include more or fewer electrodes 542. In any of these embodiments, the electrodes 542 can be selectively activated, simultaneously or sequentially, in a manner generally similar to that describe above to provide the patient with a therapeutically effective treatment.

In other embodiments, the electrode assembly can have arrangements other than those described above. For example, other electrode assemblies can have support members with shapes other than those shown in FIGS. 4 and 5, including irregular shapes. In still further embodiments, the electrodes can be distributed over the support members or irregular patterns, for example, to align with sites at the brain 120 most likely to be selected for stimulation.

Figure 6:
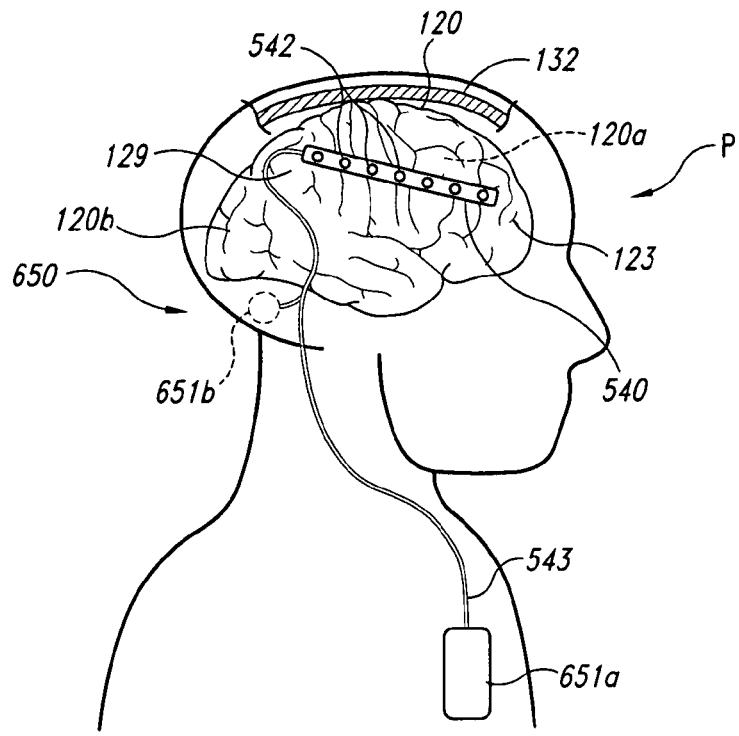
FIG. 6 is a partially schematic, side view of a patient's upper body, head and neck, along with an electrode assembly positioned in accordance with yet another embodiment of the invention.

In one aspect of embodiments described above with reference to FIGS. 4 and 5, the electrode assemblies are positioned over the left hemisphere 120a of the patient's brain because the language centers of the brain are typically concentrated there. In other embodiments, the electrode assemblies can be positioned on the right side 120b of the patient's brain 120 to stimulate right hemisphere neurons. For example, as shown in FIG. 6, an electrode assembly 540 generally similar to that described above with reference to FIG. 5 can be positioned over the right side 120b of the patient's brain 120 between the inferior frontal lobe 123 and the inferior parietal lobe 129. Accordingly, the electrode assembly 540 can be positioned adjacent to the brain structures homologous to those described above with reference to FIGS. 2-4.

In one aspect of this embodiment, the stimulation applied to the right side 120b of the patient's brain 120 can recruit right-side neurons to take over functions normally provided by (now defective) tissue on the left side 120a of the patient's brain 120. In another embodiment, (used, for example, when it is determined that recruiting homologous right-side neurons is actually detrimental to the patient's recovery of language-based functionality), the stimulation is applied to the right side 120b of the patient's brain 120 to impede or inhibit the body's attempts to recruit right-side neurons. In a particular aspect of this embodiment, the manner in which this stimulation is applied (e.g., the level of the voltage or current applied and/or the manner in which the voltage or current is varied or modulated) can determine whether the effect of the right-side neurons is enhanced or inhibited. In another embodiment, the location of the electrodes can determine whether the effect of the right-side neurons is enhanced or inhibited. In either embodiment, it can be advantageous to have a plurality of electrodes 542 (as shown in FIG. 6) available on the right side 120b of the brain 120 to allow flexibility in treating the patient's language-based disorder. The plurality of electrodes 542 can be arranged along a single axis (as shown in FIG. 6), or along multiple axes (e.g., as shown in FIG. 4), or in an irregular pattern. In still another embodiment, the foregoing technique can be used to inhibit the body's attempts to recruit left-side neurons, for example, when it is determined that recruiting such neurons is actually detrimental to the patient's recovery.

In another aspect of an embodiment shown in FIG. 6, the electrode assembly 540 can form a portion of a system 650 that also includes a pulse generator 651. For purposes of illustration, two alternative examples of pulse generators 651 are shown in FIG. 6 as a first pulse generator 651a and a second pulse generator 651b. The first pulse generator 651a can be implanted at a subclavicular location in the patient P, and the second pulse generator 651b can be implanted above the neck, posteriorly to the ear of the patient P. Either pulse generator 651 can be coupled to the electrode assembly 540 with the lead 543 and can provide electrical signals that stimulate the adjacent neurons, as described in greater detail below.

In one embodiment, the electrical signals can be applied to a single one of the electrodes 542 to provide a monopolar pulse of current to a small area of the brain 120. Accordingly, the system 650 can include a return electrode, which can be a portion of a pulse generator 651, or a separate electrode implanted elsewhere in the patient P (e.g., on the other side of the patient's brain 120 or at a subclavicular location). In other embodiments, electrical current can be passed through all of the electrodes 542 or only a subset of the electrodes 542 to activate larger or different populations of neurons. In one aspect of these embodiments, the potential applied to the electrodes 542 can be the same across all of the activated electrodes 542 to provide monopolar stimulation at the stimulation site. In other embodiments, some of the electrodes 542 can be biased with a positive polarity and other electrodes 542 can be biased with a negative polarity. This embodiment provides a bipolar stimulation to the brain 120. The particular configuration of the electrodes 542 activated during treatment can be optimized after implantation to provide the most efficacious therapy for the patient P.

The particular waveform of the applied stimulus depends upon the symptoms of the patient P. In one embodiment, the stimulus includes a series of biphasic, charge balanced pulses. In one aspect of this embodiment, each phase of the pulse is generally square. In another embodiment, the first phase can include a generally square wave portion representing an increase in current above a reference level, and a decrease below the reference level. The second phase can include a gradual rise back to the reference level. The first phase can have a pulse width ranging from about 25 microseconds to about 400 microseconds. In particular embodiments, the first phase can have a pulse width of 100 microseconds or 250 microseconds. The total pulse width can range up to 500 milliseconds.

The voltage of the stimulus can have a value of from about 0.25 V to about 10.0 V. In further particular embodiments, the voltage can have a value of from about 0.25 V to about 5.0 V, about 0.5 V to about 3.5 V, about 2.0 V to about 3.5 V or about 3 V. The voltage can be selected to be below a level that causes movement, speech or sensation in the patient (e.g., subthreshold) or above such a level (e.g., suprathreshold). In certain embodiments, the practitioner may control the current applied to the patient, in addition to or in lieu of controlling the voltage applied to the patient.

The frequency of the stimulus can have a value of from about 25 Hz to about 250 Hz. In particular embodiments, the frequency can have a value of from about 50 Hz to about 150 Hz, or about 100 Hz. The stimulation can be applied for a period of 0.5 hour-4.0 hours, and in many applications the stimulation can be applied for a period of approximately 0.5 hour-2.0 hours, either during language-based therapy (e.g., language comprehension training) or before, during and/or after such therapy. In other embodiments, the stimulation can be applied continuously, or only during waking periods but not during sleeping periods. It may be particularly effective to treat language disorders by applying stimulation before, during, and/or after language-based therapy because the language centers of the brain may be active during many periods of time in addition to active therapy periods. In particular aspects of this embodiment, the characteristics (e.g., current, voltage, waveform, pulse duration, frequency) are different depending on whether the stimulation is applied before, during or after the language-based therapy. In still further embodiments, the stimulation can be applied while a selected drug (e.g., an amphetamine or other neuroexcitatory agent) is active. In other embodiments, such drugs are not administered. Examples of specific electrical stimulation protocols for use with an electrode array at an epidural stimulation site are as follows:

EXAMPLE 1

An electrical stimulus having a current of from about 3 mA to about 10 mA, an impedance of 500 to 2000 Ohms, a pulse duration of 160 microseconds, and a frequency of approximately 100 Hz. The therapy is not applied continuously, but rather during 30-120 minute intervals, associated with language-based therapy.

EXAMPLE 2

The stimulus has a current of from about 3 mA to about 6 mA, a pulse duration of approximately 150-180 microseconds, and a frequency of approximately 25 Hz-31 Hz. The stimulus is applied continuously during waking periods, but it is discontinued during sleeping periods to conserve battery life of the implanted pulse generator.

EXAMPLE 3

The stimulus has a current of from about 3 mA to about 6 mA, a pulse duration of approximately 90 microseconds, and a frequency of approximately 30 Hz. This stimulus is applied continuously during waking and sleeping periods, but it can be selectively discontinued during sleeping periods.

In one aspect of embodiments of the systems described above with reference to FIGS. 4-6, an electrode assembly having multiple electrodes is positioned at the cortex of the brain 120. Further details of such placements are described below with reference to FIGS. 7-9. In other embodiments, portions of the electrode assemblies can extend into or beneath the cortex to stimulate interior portions of the brain 120, including deep brain tissue. In still further embodiments, the electrode assembly can include a single electrode or one or more electrode pairs, also described in greater detail below with reference to FIGS. 7-9.

Figure 7:
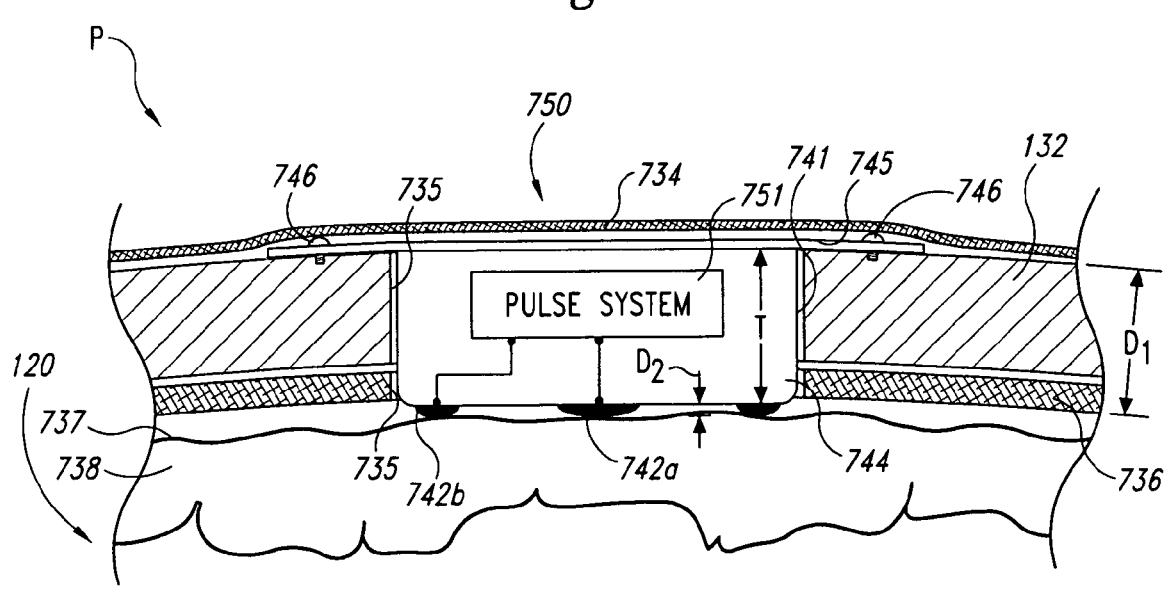
FIG. 7 is a cross-sectional illustration of an electrode system positioned in a patient's skull in accordance with an embodiment of the invention.

FIG. 7 is a cross-sectional view of a stimulation system 750 configured and implanted in accordance with an embodiment of the invention. In one aspect of this embodiment, the stimulation system includes a support member 741, an integrated pulse system 751 (shown schematically) carried by the support member 741, and first and second electrodes or contacts 742 (identified individually by reference numbers 742a and 742b). The first and second electrodes 742 are electrically coupled to the pulse system 751 and are carried by the support member 741.

The support member 741 can be configured to be implanted in the skull 132 or another region of a patient P above the neckline. In one embodiment, for example, the support member 741 includes a housing 744 and an attachment element 745 connected to the housing 741. The housing 744 can be a molded casing formed from a biocompatible material, and can have an interior cavity for carrying the pulse system 751 and a power supply. The housing 744 can alternatively be a biocompatible metal or another suitable material. The housing 744 can have a diameter of approximately 1-4 cm, and in many applications the housing 744 can be 1.5-2.5 cm in diameter. The thickness T of the housing 744 can be approximately 0.5-4 cm, and can more generally be about 1-2 cm. The housing 744 can also have other shapes (e.g., rectilinear, oval, elliptical) and other surface dimensions. The stimulation system 750 can weigh 35 g or less and/or can occupy a volume of 20 cc or less. The attachment element 745 can include a flexible cover, a rigid plate, a contoured cap, or another suitable element for holding the support member 741 relative to the skull 132 or other body part of the patient P. In one embodiment, the attachment element 745 includes a mesh, e.g., a biocompatible polymeric mesh, metal mesh, or other suitable woven material. The attachment element 745 can alternatively be a flexible sheet of Mylar, polyester, or another suitable material.

In one aspect of an embodiment shown in FIG. 7, the stimulation system 750 is implanted in the patient P by forming an opening in the scalp 734 and cutting a hole 735 completely through the skull 132. The hole 735 can also pass through the dura mater 736 for subdural applications (shown), or the hole 735 can pass through the skull 132 but not the dura mater 736 for epidural applications. The hole 735 can be sized to receive the housing 744 of the support member 741, and in most applications the hole 735 can be smaller than the attachment element 745. A practitioner can insert the support member 741 into the hole 735 and then secure the attachment element 745 to the skull 132. The attachment element 745 can be secured to the skull 132 using a plurality of fasteners 746 (e.g., screws, spikes, etc.) or an adhesive. In another embodiment, a plurality of downwardly depending spikes can be formed integrally with the attachment element 745 to provide anchors that can be driven into the skull 132.

The embodiment of the stimulation system 750 shown in FIG. 7 is configured to be implanted in the patient P so that the electrodes 742 are juxtaposed to a desired cortical stimulation site. The housing 744 can project from the attachment element 745 by a distance $D_1$ such that the electrodes 742 are positioned at least proximate to the dura mater 736 or the pia mater 737 surrounding the cortex 738. The electrodes 742 can project from the housing 744 as shown in FIG. 7. In the particular embodiment shown in FIG. 7, the electrodes 742 project from the housing 744 by a distance $D_2$ so that the electrodes 742 press against a desired surface of the brain 120. The distance $D_2$ is from 0.1 mm to about 5 cm in some embodiments, and has other values in other embodiments. In still further embodiments, the electrodes 742 are flush with the housing 744. The electrodes 742 can be separate conductive members attached to the housing 744, or the electrodes 742 can be integral surface regions of the housing 744.

The configuration of the stimulation system 750 is not limited to the embodiment shown in FIG. 7. For example, in other embodiments, the housing 744, and the attachment element 745 can be configured to position the electrodes 742 in several different regions of the brain. In particular embodiments, the housing 744 and the attachment element 745 can be configured to position the electrodes 742 deep within the cortex 738 or against the dura mater 736.

The pulse system 751 shown in FIG. 7 generates and/or transmits electrical pulses to the electrodes 742 to stimulate a cortical region of the brain 120. The particular embodiment of the pulse system 751 shown in FIG. 7 is an "integrated" unit in that the pulse system 751 is carried by the support member 741. The pulse system 751, for example, can be positioned within the housing 744 so that the electrodes 742 can be carried by the housing 744 and connected directly to the pulse system 751 without having external leads outside the stimulation system 750. The distance between the electrodes 742 and the pulse system 751 can be less than 4 cm, for example, 0.10 to 2.0 cm. The stimulation system 750 can accordingly provide electrical pulses to the stimulation site without requiring a remote implanted pulse generator, which is connected to the electrodes 742 with surgically tunneled cables. In other embodiments, the pulse generator can be implanted separately from the electrodes, for example, in a manner generally similar to that described above with reference to FIG. 6. In still further embodiments, signals can be transmitted to the electrodes 742 from a remote location outside the patient's body via a wireless (e.g., RF) link.

Figure 8:
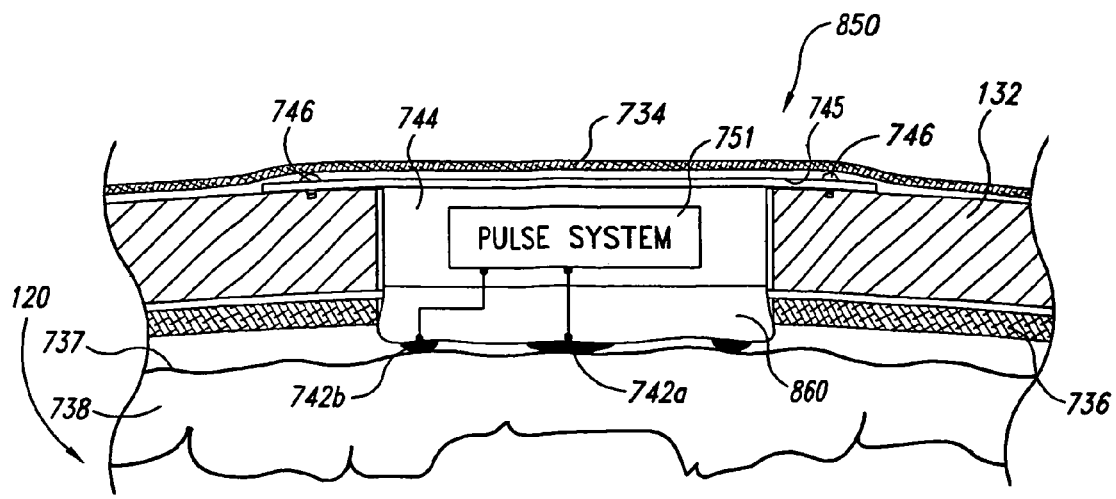
FIG. 8 is a partially schematic cross-sectional side view of an electrode system positioned in a patient's skull and having an electrode urged against a portion of the patient's brain in accordance with another embodiment of the invention.

FIG. 8 is a cross-sectional view of a stimulation system 850 configured and implanted in accordance with an embodiment of the invention. In one aspect of this embodiment, the stimulation system 850 includes a driving element 860 coupled to the electrodes 742 to mechanically urge the electrodes 742 away from the housing 744. In another embodiment, the driving element 860 can be positioned between the housing 744 and the attachment element 745, and the electrodes 742 can be attached directly to the housing 744. The driving element 860 can include a compressible member, for example, an open or closed cell biocompatible compressible foam, or a compressible solid (e.g., silicon rubber). In other embodiments, the driving element 860 can include a fluid-filled bladder, a spring, or any other suitable element that resiliently and/or elastically exerts a force against the electrodes 742.

In one aspect of an embodiment shown in FIG. 8, the driving element 860 is compressed slightly upon implantation so that the electrodes 742 contact the stimulation site. For example, the compressed driving element 860 can gently press the electrodes 742 against the surface of the pia mater 737. It is expected that the driving element 860 will provide a uniform, consistent contact between the electrodes 742 and the pial surface of the cortex 738. The stimulation system 850 is expected to be particularly useful when the implantable device is attached to the skull 132 and the stimulation site is on the pia mater 737 or the dura mater 736. It can be difficult to position the electrodes 742 against the pia mater 737 because the distance between the skull 132 and the dura mater 736 or the pia mater 737 varies as the brain 120 expands and contracts relative to the skull 132, and also because this distance varies from one patient P to another. The driving element 860 of the stimulation system 850 can compensate for the different distances between the skull 132 and the pia mater 737 so that a single type of device can better fit several different patients P. Moreover, the driving element 860 can change the position of the electrodes 742 as the brain 120 moves within the skull 132.

Figure 9:
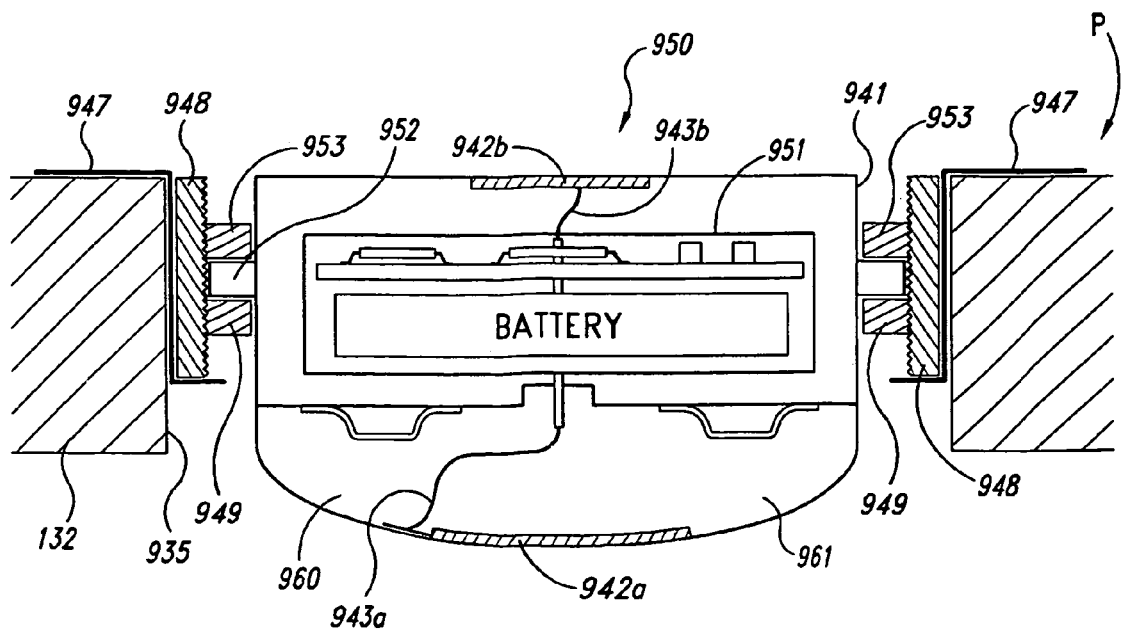
FIG. 9 is a partially schematic, side elevational view of an electrode system positioned in the patient's skull in accordance with still another embodiment of the invention.
Figure 10:
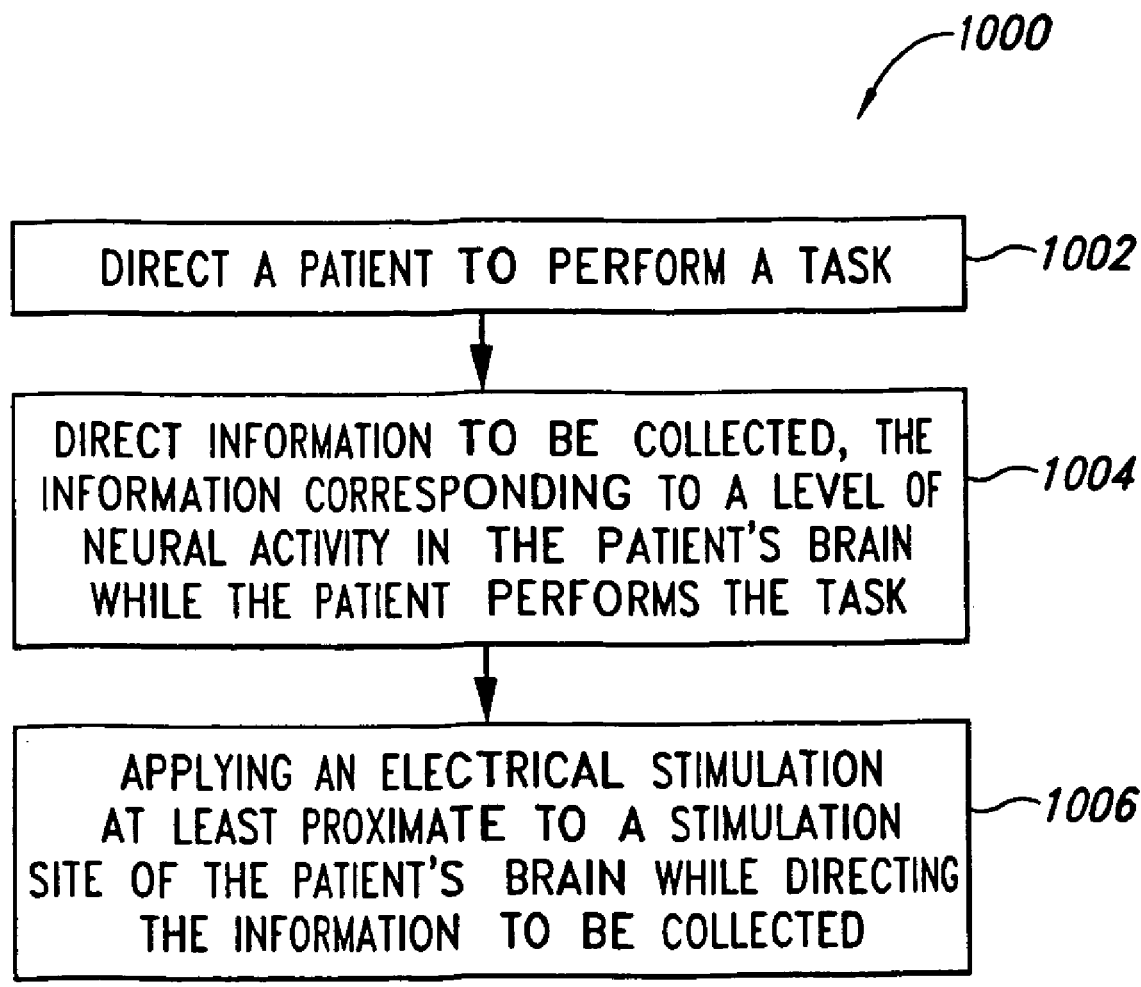
FIG. 10 is a flow chart illustrating a method for collecting information while stimulating a patient's brain in accordance with another embodiment of the invention.

FIG. 9 is a cross-sectional view of a stimulation system 950 configured and implanted in accordance with another embodiment of the invention. The stimulation system 950 can include a support member 941, an integrated pulse system 951 (shown schematically) carried by the support member 941, a driving element 960 carried by the support member 941, and an electrode or contact 942a carried by the driving element 960. The contact 942a is electrically coupled to the pulse system 951 by a lead 943a. The driving element 960 can be a compliant material having a cavity 961 filled with a fluid such as saline or air. In another embodiment, the stimulation system 950 can further include an optional return electrode 942b carried on the opposite side of the support structure 941. The return electrode 942b can be electrically coupled to the pulse system 951 by a return lead 943b.

To implant the stimulation apparatus 960, a burr hole 935 is cut completely through the skull 132 of the patient P at a predetermined location identified according to the methods set forth above. The burr hole 935 can also pass through the dura mater (not shown FIG. 9). After forming the burr hole 935, a ferrule 947 is placed in the burr hole 935, and a threaded barrel 948 is welded or otherwise attached to the ferrule 947. A position ring 949 is then threaded along the threads of the barrel 948 to a desired height. The stimulation system 950 is placed in the burr hole 935 until a rim 952 projecting from the support member 941 engages the position ring 949. A lock ring 953 is then threaded onto the barrel 949 until it engages the rim 952. The position ring 949 and the lock ring 953 hold the support member 941 at a desired height relative to the surface of the patient's brain 120.

In one aspect of the embodiments described above with reference to FIGS. 1A-9, information is collected on the activity of the brain prior to implanting any of the foregoing stimulation systems. Accordingly, the collected information can guide the practitioner as the practitioner determines where to apply the stimulation. In a method in accordance with another embodiment of the invention (shown in FIG. 10), such information can be collected while the stimulation system is activated. For example, a method 1000 in accordance with an embodiment of the invention includes directing a patient to perform a task (process portion 1002), directing information to be collected corresponding to a level of neural activity in the patient's brain while the patient performs the task (process portion 1004), and applying an electrical stimulation to the patient's brain while directing the information to be collected (process portion 1006). In one aspect of this embodiment, the task performed by the patient can be a language-based task, for example, any of the tasks described above with reference to FIGS. 1A-1B. In another embodiment, the task can be another type of task (for example, a motor task) which also generates a detectable response in the patient's brain. In any of these embodiments, the information can take the form of visually accessible images (e.g., using fMRI, MRI, CT, or PET techniques), or the information can take other forms that are not necessarily visually accessible.

The information collected while the stimulation system is active can be used to determine whether the stimulation system is creating the desired response in the patient's brain, and/or whether the response is occurring in the desired area of the patient's brain. This technique can be used to provide feedback on the efficacy of the stimulation system and can also be used to adjust aspects of the stimulation system. For example, when the stimulation system includes a plurality of electrodes, the foregoing technique can be used to determine which of the electrodes is providing the desired response. This technique can also be used to determine whether the voltage level (and/or the variation of the voltage level) of the signals applied to the electrodes produces the desired effect. Accordingly, such techniques can be used in addition to or in lieu of receiving direct feedback from the patient to determine the efficacy of the treatment. Such techniques can also be used to tailor the manner in which the treatment is administered.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

The invention claimed is:

1. A method for selecting a stimulation site in a language-disorder patient, comprising:
   administering a neuroexcitatory drug to a patient;
   directing a patient to perform a language-based task, including directing the patient to repeat a noun;
   directing information to be collected while the patient performs the language-based task with the neuroexcitatory drug active in the patient's body, the information corresponding to a level of neural activity in the patient's brain while the patient performs the language-based task; and
   based at least in part on the information, selecting a stimulation site within the patient's skull, proximate the dura mater, and outside a cortical surface of the patient's brain for receiving an electrode coupleable to an electrical current.

2. A method for selecting a stimulation site in a language-disorder patient, comprising:
   administering a neuroexcitatory drug to a patient;
   directing the patient to perform a language-based task;
   directing information to be collected, the information corresponding to a level of neural activity in the patient's brain while the patient performs the language-based task with the neuroexcitatory drug active in the patient's body; and
   based at least in part on the information, selecting a stimulation site within the patient's skull for receiving an electrode coupleable to an electrical current.

3. The method of claim 2 wherein selecting a stimulation site includes selecting a stimulation site at least proximate to at least one of Broca's area, Wernicke's area, and neuronal connections extending between Broca's area and Wernicke's area.

4. The method of claim 2 wherein selecting a stimulation site includes selecting a stimulation site at least proximate to at least one of the middle temporal gyrus, the retrosplenial cortex and the retrosplenial cuneus of the brain.

5. The method of claim 2 wherein directing the patient to perform a language-based task includes directing the patient to perform a task that requires no verbal output.

6. The method of claim 2 wherein directing the patient to perform a language-based task includes directing the patient to silently generate a verb associated with a common noun.

7. The method of claim 2 wherein directing the patient to perform a language-based task includes directing the patient to retrieve a word based on a letter cue.

8. The method of claim 2 wherein directing the patient to perform a language-based task includes directing the patient to retrieve a word based on a visual cue.

9. The method of claim 2 wherein directing the patient to perform a language-based task includes directing the patient to respond nonverbally to an oral task that requires the patient to understand the difference between two auditory commands.

10. The method of claim 2, further comprising implanting an electrode at least proximate to the stimulation site.

11. The method of claim 2 wherein directing information to be collected includes directing a computer-based routine to collect the information.

12. The method of claim 2, further comprising directing the formation of an image of at least a portion of the patient's brain, with at least a portion of the image having features representative of the information.

13. The method of claim 2 wherein directing information to be collected includes directing the formation an image of at least a portion of the patient's brain, the image including a first region with a characteristic of the first region having a first value, the image further including a second region with a characteristic of the second region having a second value different than the first value.

14. The method of claim 2 wherein directing a patient to perform a language-based task includes directing the patient to perform a first language-based task and wherein directing information to be collected includes directing first information to be collected while the patient performs the first language-based task, and wherein the method further comprises:
   directing the patient to perform a second language-based task;
   directing second information to be collected while the patient performs the second language-based task; and
   determining a location for the stimulation site based on both the first information and the second information.

15. The method of claim 2 wherein directing a patient to perform a language-based task includes directing the patient to perform a first language-based task subject to a language disorder and wherein directing information to be collected includes directing first information to be collected while the patient performs the first language-based task, and wherein the method further comprises:
   monitoring a first image of the patient's brain function while the patient performs the first language-based task;
   identifying a second language-based task subject to a language disorder;
   monitoring a second image of the patient's brain function while the patient performs the second language-based task; and
   comparing the first and second images to identify at least one stimulation site of the brain.

16. The method of claim 2, further comprising:
   positioning at least one electrode at the stimulation site;
   coupling the at least one electrode to a source of electrical potential; and
   at least reducing a language disorder of the patient by applying electrical stimulation directly to the stimulation site via the at least one electrode while not actively engaging the patient in a language-based task.

17. The method of claim 16 wherein positioning at least one electrode includes implanting the at least one electrode.

18. The method of claim 16 wherein applying an electrical stimulation includes applying an electrical stimulation to the left hemisphere of the brain.

19. The method of claim 16 wherein applying an electrical stimulation includes applying an electrical stimulation to the right hemisphere of the brain.

20. The method of claim 16 wherein at least reducing a language disorder of the patient includes at least reducing an aphasia of the patient.

21. The method of claim 16 wherein applying an electrical stimulation includes applying an electrical stimulation at least proximate to at least one of Broca's area, Wernicke's area, and neuronal connections extending between Broca's area and Wernicke's area.

22. The method of claim 16 wherein applying an electrical stimulation includes applying an electrical stimulation to at least one of the middle temporal gyrus, the retrosplenial cortex and the retrosplenial cuneus of the brain.

23. The method of claim 16, further comprising:
   administering a neuroexcitatory agent to the patient; and
   applying the electrical stimulation while the neuroexcitatory agent is active in the patient's body.

24. The method of claim 16 wherein applying electrical stimulation includes applying electrical stimulation below a level that causes movement, speech or sensation in the patient.

25. The method of claim 16 wherein applying electrical stimulation includes applying electrical stimulation at or above a level that causes movement, speech or sensation in the patient.

26. The method of claim 16 wherein at least reducing a language disorder includes eliminating the language disorder.

27. The method of claim 16, further comprising locating the stimulation site relative to an anatomical feature of the patient.

28. The method of claim 16, further comprising locating the stimulation site relative to a fiducial having a fixed location relative to the patient's skull.

29. The method of claim 16 wherein applying an electrical stimulation includes applying a varying electrical stimulation signal having a frequency of from about 5 Hz to about 200 Hz.

30. The method of claim 16 wherein applying an electrical stimulation includes applying a varying electrical stimulation signal having an electrical potential of from about 0.25 volts to about 5.0 volts.

31. The method of claim 2 wherein directing information to be collected includes directing information to be collected corresponding to blood oxygen levels in the brain.

32. The method of claim 2, further comprising placing an electrode at least proximate to the stimulation site.

33. The method of claim 2 wherein directing information to be collected includes directing the collection of functional magnetic resonance image data.

34. The method of example 2, further comprising implanting an electrode at least proximate to the stimulation site and applying an electrical stimulation via the electrode.

35. The method of claim 2, further comprising
   applying electrical stimulation to the patient's brain while directing the information to be collected.

36. The method of claim 2 wherein
   directing the patient to perform a task includes directing the patient to retrieve a word based on a letter cue, and wherein the method further comprises
   applying electrical stimulation to the patient's brain while directing the information to be collected.

37. The method of claim 2, further comprising
   locating the stimulation site relative to a fiducial having a fixed location relative to the patient's skull.

38. A method for treating a language disorder, comprising:
   administering a neuroexcitatory drug to a patient;
   directing the patient to perform a language-based task, including directing the patient to retrieve a word based on a letter cue;
   directing information to be collected while the patient performs the language-based task with the neuroexcitatory drug active in the patient's body, the information corresponding to a level of neural activity in the patient's brain while the patient performs the language-based task; and at least reducing a language disorder of the patient by applying an electrical stimulation at least proximate to one or more stimulation sites, with locations of all the stimulation sites for receiving electrical stimulation at the patient's brain being based at least in part on the information, and being proximate the dura mater and outside a cortical surface of the patient's brain.

39. The method of claim 38 wherein directing the patient to perform a language-based task includes directing the patient to perform a task that requires no verbal output.

40. The method of claim 38 wherein directing the patient to perform a language-based task includes directing the patient to silently generate a verb associated with a common noun.

41. The method of claim 38 wherein directing the patient to perform a language-based task includes directing the patient to repeat a noun.

42. The method of claim 38 wherein directing the patient to perform a language-based task includes directing the patient to retrieve a word based on a visual cue.

43. The method of claim 38 wherein directing the patient to perform a language-based task includes directing the patient to respond nonverbally to an oral task that requires the patient to understand the difference between two auditory commands.

44. The method of claim 38, further comprising:
administering a neuroexcitatory agent to the patient; and
applying the electrical stimulation while the neuroexcitatory agent is active in the patient's body.

45. The method of claim 38 wherein directing information to be collected includes directing a computer-based routine to collect the information.

46. The method of claim 38, further comprising directing the formation of an image of at least a portion of the patient's brain, with at least a portion of the image having features representative of the information.

47. The method of claim 38 wherein directing information to be collected includes directing the formation an image of at least a portion of the patient's brain, the image including a first region with a characteristic of the first region having a first value, the image further including a second region with a characteristic of the second region having a second value different than the first value.

48. The method of claim 38, further comprising implanting at least one electrode at least proximate to the stimulation site, and wherein applying an electrical stimulation includes applying an electrical signal to the at least one electrode.

49. The method of claim 38 wherein directing a patient to perform a language-based task includes directing the patient to perform a first language-based task and wherein directing information to be collected includes directing first information to be collected while the patient performs the first language-based task, and wherein the method further comprises:
directing the patient to perform a second language-based task;
directing second information to be collected while the patient performs the second language-based task; and
determining a location for the stimulation site based on both the first information and the second information.

50. A method for treating a language disorder, comprising:
administering a neuroexcitatory drug to a patient;
directing the patient to perform a language-based task;
directing information to be collected while the patient performs the language-based task with the neuroexcitatory drug active in the patient's body, the information corresponding to a level of neural activity in the patient's brain while the patient performs the language-based task; and
at least reducing a language disorder of the patient by applying an electrical stimulation at least proximate to a stimulation site, the location of the stimulation site being based at least in part on the information.

51. The method of claim 50 wherein:
directing a patient to perform a language-based task includes directing the patient to respond nonverbally to an oral task that requires the patient to understand the difference between two auditory commands.

52. The method of claim 50 wherein directing the patient to perform a task includes directing the patient to perform a language-based task that requires no verbal output.

53. The method of claim 50 wherein directing the patient to perform a task includes directing the patient to silently generate a verb associated with a common noun.

54. The method of claim 50 wherein directing the patient to perform a task includes directing the patient to repeat a noun.

55. The method of claim 50 wherein directing the patient to perform a task includes directing the patient to retrieve a word based on a letter cue.

56. The method of claim 50 wherein directing the patient to perform a task includes directing the patient to retrieve a word based on a visual cue.

57. The method of claim 50, further comprising
not engaging the patient in a speech therapy task while applying the electrical stimulation.

* * * * *